United States Patent
Zhang et al.

(10) Patent No.: US 10,328,274 B2
(45) Date of Patent: Jun. 25, 2019

(54) SYSTEM AND METHOD FOR IDENTIFYING AND RESPONDING TO P-WAVE OVERSENSING IN A CARDIAC SYSTEM

(71) Applicant: Medtronic, Inc., Minneapolis, MN (US)

(72) Inventors: Xusheng Zhang, Shoreview, MN (US); Paul J. Degroot, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 107 days.

(21) Appl. No.: 15/495,104

(22) Filed: Apr. 24, 2017

(65) Prior Publication Data

US 2017/0354827 A1   Dec. 14, 2017

Related U.S. Application Data

(60) Provisional application No. 62/347,177, filed on Jun. 8, 2016.

(51) Int. Cl.
*A61N 1/00* (2006.01)
*A61N 1/39* (2006.01)
(Continued)

(52) U.S. Cl.
CPC .............. *A61N 1/3956* (2013.01); *A61B 5/00* (2013.01); *A61B 5/04012* (2013.01);
(Continued)

(58) Field of Classification Search
CPC ..... A61B 5/00; A61B 5/04012; A61B 5/0456; A61B 5/0464; A61N 1/36507; A61N 1/3704; A61N 1/3956; A61N 1/3987
See application file for complete search history.

(56) References Cited

U.S. PATENT DOCUMENTS 5,354,316 A   10/1994   Keimel
5,545,186 A   8/1996   Olson et al.
(Continued)

FOREIGN PATENT DOCUMENTS

WO   2006104849 A1   10/2006

OTHER PUBLICATIONS

Cao et al., "Multi-threshold sensing of cardiac electrical signals in an extracardiovascular implantable cardioverter defibrillator", U.S. Appl. No. 15/142,171, filed Apr. 29, 2016, 71 pages.
(Continued)

*Primary Examiner* — George Manuel

(57) ABSTRACT

A cardiac medical system, such as an implantable cardioverter defibrillator (ICD) system, receives a cardiac electrical signal by and senses cardiac events when the signal crosses an R-wave sensing threshold. The system determines at least one sensed event parameter from the cardiac electrical signal for consecutive cardiac events sensed by the sensing circuit and compares the sensed event parameters to P-wave oversensing criteria. The system detects P-wave oversensing in response to the sensed event parameters meeting the P-wave oversensing criteria; and adjusts at least one of an R-wave sensing control parameter or a therapy delivery control parameter in response to detecting the P-wave oversensing.

32 Claims, 16 Drawing Sheets

(51) Int. Cl.
  *A61B 5/04*     (2006.01)
  *A61B 5/0456*   (2006.01)
  *A61B 5/0464*   (2006.01)
  *A61B 5/00*     (2006.01)
  *A61N 1/365*    (2006.01)
  *A61N 1/37*     (2006.01)

(52) U.S. Cl.
  CPC .......... *A61B 5/0456* (2013.01); *A61B 5/0464* (2013.01); *A61N 1/36507* (2013.01); *A61N 1/3987* (2013.01); *A61N 1/3704* (2013.01)

(56) References Cited

U.S. PATENT DOCUMENTS

| | | |
|---|---|---|
| 5,658,320 A | 8/1997 | Betzold et al. |
| 6,393,316 B1 | 5/2002 | Gillberg et al. |
| 6,539,259 B1 | 3/2003 | Weinberg et al. |
| 7,027,858 B2 | 4/2006 | Cao et al. |
| 7,031,771 B2 | 4/2006 | Brown et al. |
| 7,139,604 B1 | 11/2006 | Mouchawar et al. |
| 7,333,855 B2 | 2/2008 | Gunderson et al. |
| 7,761,150 B2 | 7/2010 | Ghanem et al. |
| 7,937,135 B2 | 5/2011 | Ghanem et al. |
| 8,055,342 B2 | 11/2011 | Zhang et al. |
| 8,160,684 B2 | 4/2012 | Ghanem et al. |
| 8,386,024 B2 | 2/2013 | Gunderson et al. |
| 8,437,842 B2 | 5/2013 | Zhang et al. |
| 8,825,145 B1 | 9/2014 | Zhang |
| 8,965,505 B2 | 2/2015 | Charlton et al. |
| 8,983,586 B2 | 3/2015 | Zhang |
| 9,002,443 B2 | 4/2015 | Zhang et al. |
| 9,168,380 B1 | 10/2015 | Greenhut et al. |
| 9,561,005 B2 | 2/2017 | Zhang |
| 9,597,525 B2 | 3/2017 | Cao et al. |
| 2012/0226179 A1* | 9/2012 | Stadler ................ A61N 1/3622 600/516 |
| 2015/0306375 A1 | 10/2015 | Marshall et al. |
| 2015/0306410 A1 | 10/2015 | Marshall et al. |
| 2016/0158567 A1 | 6/2016 | Marshall et al. |
| 2016/0213941 A1 | 7/2016 | Zhang |

OTHER PUBLICATIONS

Swerdlow, et al., "Advanced ICD Troubleshooting: Part I", PACE, Dec. 2005; vol. 28, 25 pages.
(PCT/US2017/035417) PCT Notification of Transmittal of the International Search Report and the Written Opinion of the International Searching Authority, dated Sep. 8, 2017, 10 pages.

\* cited by examiner

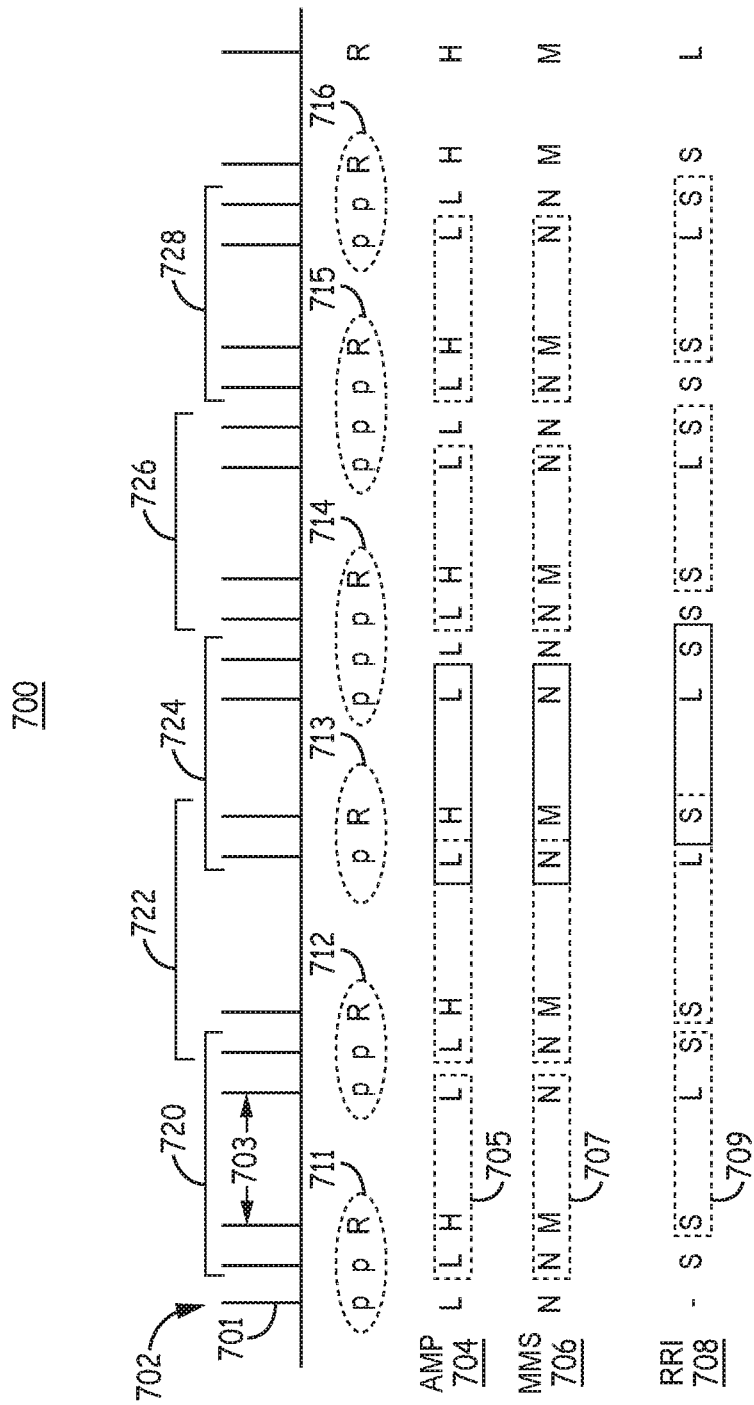

SYSTEM AND METHOD FOR IDENTIFYING AND RESPONDING TO P-WAVE OVERSENSING IN A CARDIAC SYSTEM

RELATED APPLICATIONS

This application claims the benefit of the filing date of a provisional U.S. Application Ser. No. 62/347,177, filed Jun. 8, 2016, which is incorporated by reference herein in its entirety.

TECHNICAL FIELD

The disclosure relates generally to a cardiac system and a method for identifying and responding to P-wave oversensing (PWOS).

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. The ICD may sense the cardiac electrical signals in a heart chamber and deliver electrical stimulation therapies to the heart chamber using electrodes carried by transvenous medical electrical leads. Cardiac signals sensed within the heart generally have a high signal strength and quality for reliably sensing cardiac electrical events, such as R-waves. In other examples, a non-transvenous lead may be coupled to the ICD, in which case cardiac signal sensing presents new challenges in accurately sensing cardiac electrical events.

SUMMARY

In general, the disclosure is directed to techniques for identifying P-wave oversensing by an implantable cardioverter defibrillator (ICD) and responding to the PWOS, for example by adjusting an R-wave sensing control parameter and/or adjusting a therapy control parameter. An ICD operating according to the techniques disclosed herein detects PWOS based on analysis of a cardiac electrical signal received by an extra-cardiovascular sensing electrode vector. In some examples, clusters of sensed cardiac events are detected as evidence of PWOS.

In one example, the disclosure provides an extra-cardiovascular ICD system including a sensing circuit, a therapy delivery circuit and a control circuit. The sensing circuit is configured to receive a cardiac electrical signal from electrodes coupled to the ICD and sense a cardiac event in response to the cardiac electrical signal crossing an R-wave sensing threshold. The therapy delivery circuit is configured to deliver electrical stimulation therapy to a patient's heart via electrodes coupled to the ICD. The control circuit is configured to determine at least one sensed event parameter from the cardiac electrical signal for each one of a plurality of consecutive cardiac events sensed by the sensing circuit, compare the sensed event parameters to P-wave oversensing criteria, detect P-wave oversensing in response to the sensed event parameters meeting the P-wave oversensing criteria, and adjust an R-wave sensing control parameter and/or a therapy delivery control parameter in response to detecting the P-wave oversensing.

In another example, the disclosure provides a method performed by an extra-cardiovascular implantable cardioverter defibrillator (ICD) system. The method includes receiving a cardiac electrical signal by a sensing circuit via electrodes coupled to the ICD, sensing a cardiac event in response to the cardiac electrical signal crossing an R-wave sensing threshold, determining by a control circuit of the ICD at least one sensed event parameter from the cardiac electrical signal for each one of consecutive cardiac events sensed by the sensing circuit, comparing the sensed event parameters to P-wave oversensing criteria, detecting P-wave oversensing in response to the sensed event parameters meeting the P-wave oversensing criteria; and adjusting at least one of an R-wave sensing control parameter or a therapy delivery control parameter in response to detecting the P-wave oversensing.

In another example, the disclosure provides a non-transitory, computer-readable storage medium comprising a set of instructions which, when executed by a control circuit of an ICD system, cause the system to receive a cardiac electrical signal by a sensing circuit via electrodes coupled to the ICD, sense a cardiac event in response to the cardiac electrical signal crossing an R-wave sensing threshold, determine by a control circuit of the ICD at least one sensed event parameter from the cardiac electrical signal for each one of a plurality of consecutive cardiac events sensed by the sensing circuit, compare the sensed event parameters to P-wave oversensing criteria, detect P-wave oversensing in response to the sensed event parameters meeting the P-wave oversensing criteria, and adjust an R-wave sensing control parameter and/or a therapy delivery control parameter in response to detecting the P-wave oversensing.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 14 is a timing diagram of sensed event signals that may be produced by the ICD sensing circuit and received by the ICD control circuit and illustrates techniques for detecting PWOS.

DETAILED DESCRIPTION

Figure 1A:
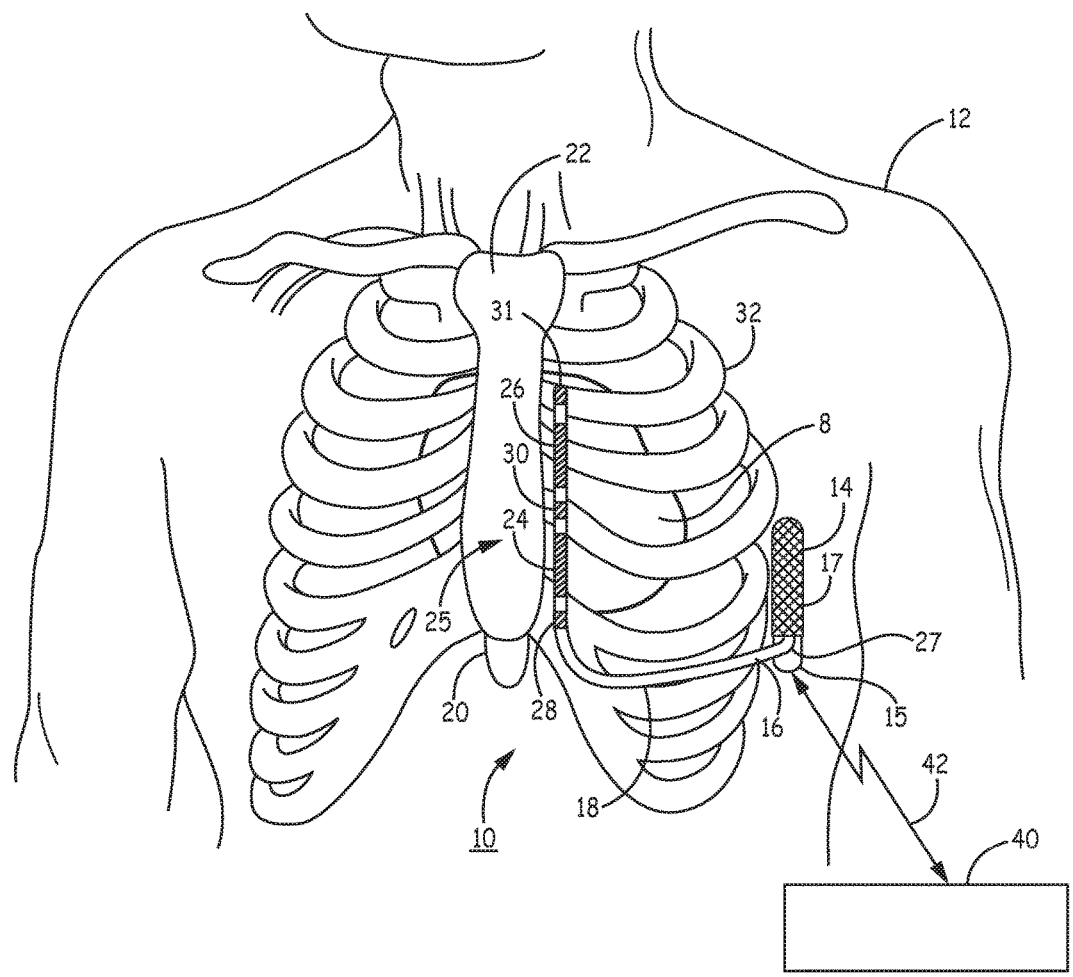
FIGS. 1A and 1B are conceptual diagrams of an extra-cardiovascular ICD system according to one example.

In general, this disclosure describes techniques for sensing cardiac electrical signals using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for identifying PWOS in an extra-cardiovascular ICD system. The term "P-wave oversensing" or "PWOS" as used herein refers to falsely sensing an R-wave by the sensing circuitry of an extra-cardiovascular ICD or pacemaker when an intrinsic P-wave occurs. P-waves, attendant to atrial depolarization, are typically small in amplitude relative to R-waves, attendant to ventricular depolarization, and therefore typically have a peak amplitude less than an R-wave sensing threshold and do not interfere with reliable R-wave sensing. When a cardiac electrical signal is being acquired using extra-cardiovascular electrodes, however, PWOS can occur, particularly when the amplitude of the R-waves is relatively small or when the heart rate is slow. Reliable R-wave sensing is important in detecting ventricular arrhythmias.

If P-waves are oversensed as R-waves, the heart rate may be over-estimated, leading to a false heart rhythm determination. For example, if the patient's heart rate is very slow and bradycardia pacing is required, PWOS may cause the ventricular rate to appear within a normal range to the ICD, resulting in withholding of bradycardia pacing pulses that may be needed to maintain a normal heart rate without hemodynamic insufficiency. If the patient's heart is in a normal range but PWOS is occurring, the heart rate may appear faster than it actually is, and the ICD may detect a ventricular tachyarrhythmia, which may lead to unnecessary tachyarrhythmia therapy being delivered, such as anti-tachycardia pacing (ATP) or one or more cardioversion/defibrillation shocks. The techniques disclosed herein for identifying PWOS enables identified PWOS to be rejected or ignored in determining a heart rhythm so that the ICD may provide an appropriate therapy delivery response.

The PWOS detection techniques are described in conjunction with an ICD coupled to implantable medical lead carrying extra-cardiovascular electrodes used for sensing cardiac electrical signals. Aspects disclosed herein for identifying and responding to PWOS, however, may be utilized in conjunction with a variety of implantable or external devices that utilize other cardiac electrical sensing lead or electrode systems. For example, the techniques for PWOS as described in conjunction with the accompanying drawings may be implemented in any implantable or external medical device enabled for sensing cardiac electrical signals, including implantable pacemakers, ICDs, CRT-Ps, CRT-Ds or cardiac monitors coupled to transvenous or epicardial leads carrying sensing electrodes; leadless pacemakers, ICDs, CRT-Ps, CRT-Ds or cardiac monitors having housing-based sensing electrodes; and external pacemakers, defibrillators, or cardiac monitors coupled to external, surface or skin electrodes.

Figure 1B:
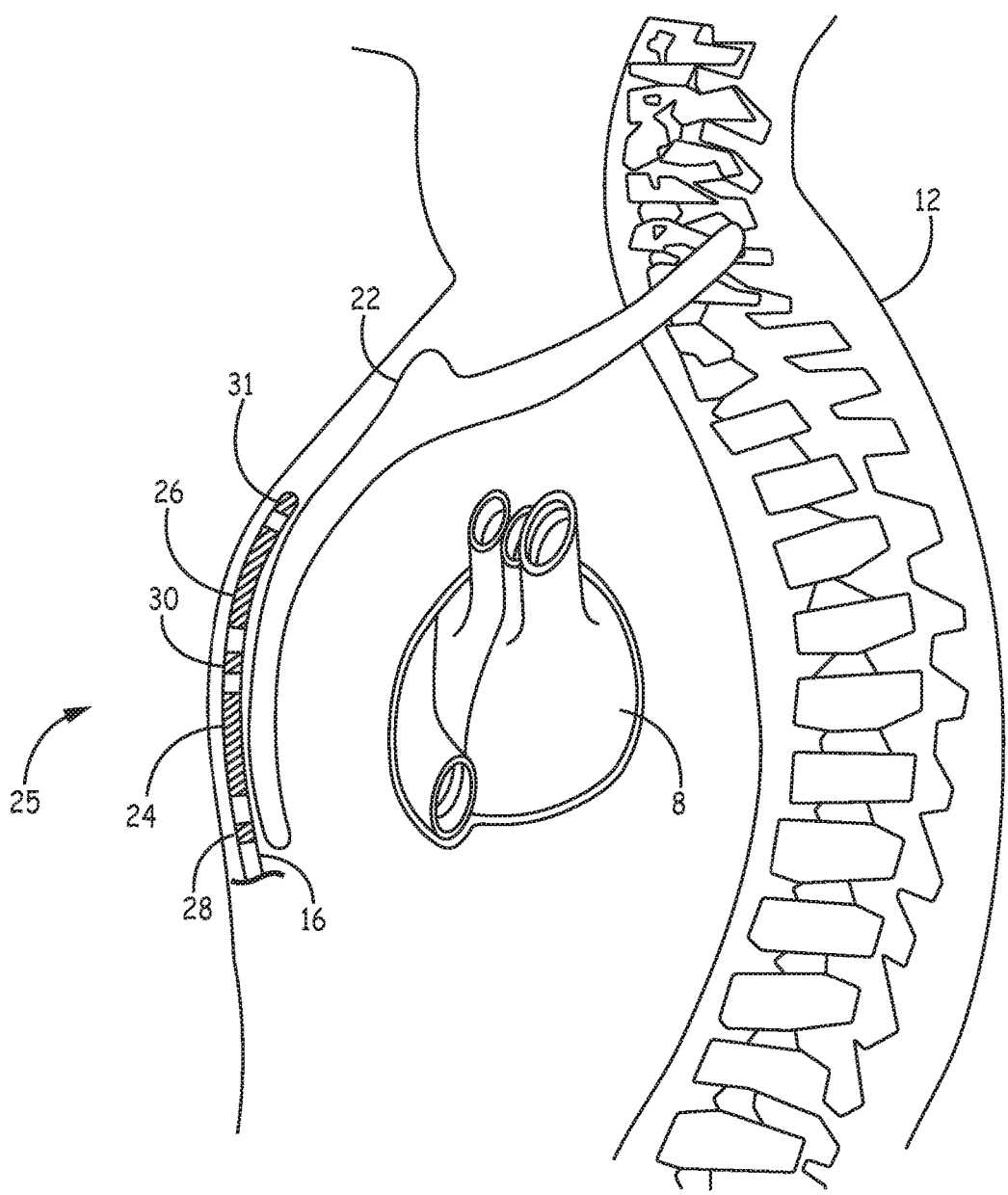

FIGS. 1A and 1B are conceptual diagrams of an extra-cardiovascular ICD system 10 according to one example. FIG. 1A is a front view of ICD system 10 implanted within patient 12. ICD system 10 includes an ICD 14 connected to an extra-cardiovascular electrical stimulation and sensing lead 16. FIG. 1B is a side view of the distal portion 25 of lead 16 implanted within patient 12. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. Electrodes 24 and 26 may be used in a pacing electrode vector for delivering extra-cardiovascular pacing pulses, such as ATP pulses, post-shock pacing pulses or bradycardia pacing pulses, and/or in a sensing electrode vector used to sense cardiac electrical signals and detect ventricular tachycardia (VT) and ventricular fibrillation (VF).

Electrodes 28, 30 and 31 are relatively smaller surface area electrodes (compared to defibrillation electrodes 24 and 26) for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may optionally be located distal to defibrillation electrode 26. In other examples, one or more pace/sense electrodes may be carried by lead 16 and be located proximal to defibrillation electrode 24, between defibrillation electrodes 24 and 26, and/or distal to defibrillation electrode 26.

Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31. Each of pacing and sensing electrodes 28, 30 and 31 are coupled to respective electrical conductors, which may be separate respective conductors within the lead body. The respective conductors electrically couple the electrodes 24, 26, 28, 30 and 31 to circuitry of ICD 14, such as a therapy delivery circuit and/or a sensing circuit as described below, via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing electrode vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30, and ATP pulses and other pacing pulses are delivered between pace/sense electrode 30 used as a cathode electrode and defibrillation electrode 24 used as a return anode electrode. In other examples, pacing pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and pacing electrode vectors may be selected according to individual patient need.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. Various example configurations of extra-cardiovascular leads and electrodes and dimensions that may be implemented in conjunction with the extra-cardiovascular sensing techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac rhythm detection parameters and therapy control parameters used by ICD 14. Control parameters used to identify PWOS according to techniques disclosed herein may be programmed into ICD 14 using external device 40. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

Figure 2A:
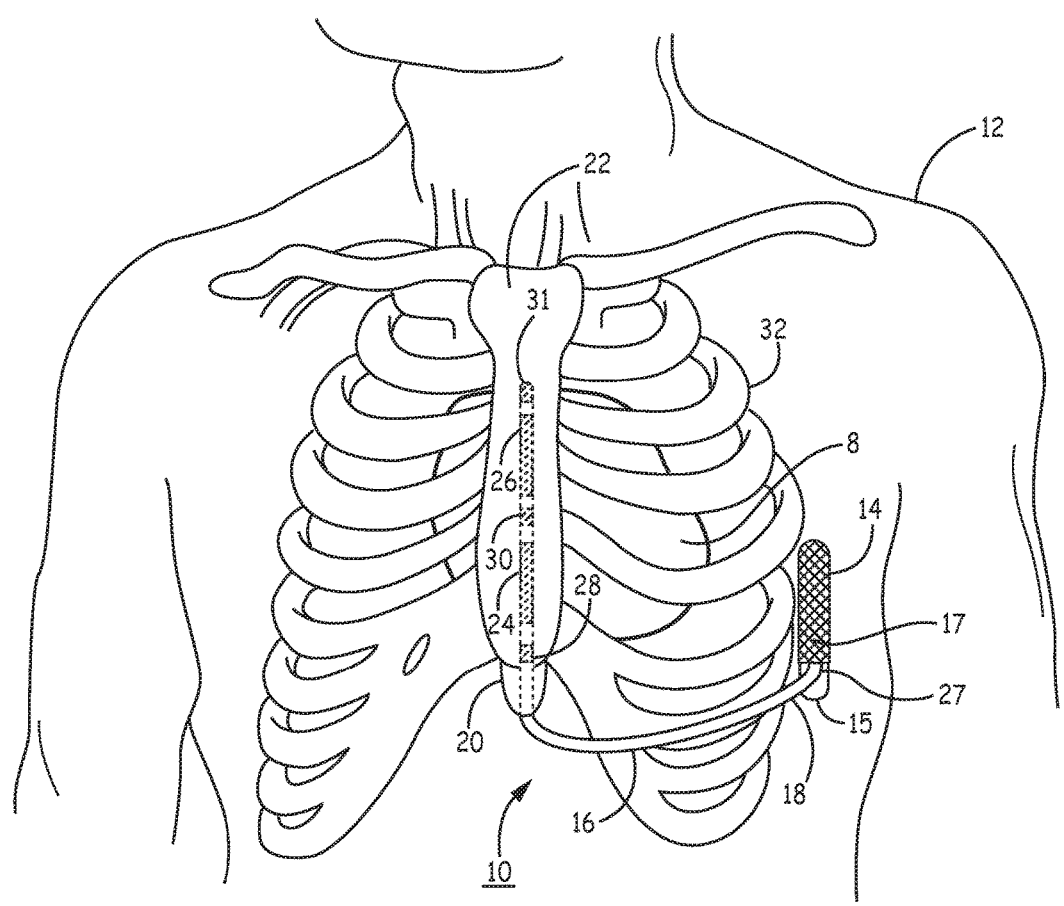
FIGS. 2A-2C are conceptual diagrams of a patient implanted with the extra-cardiovascular ICD system of FIG. 1A in a different implant configuration.
Figure 2B:
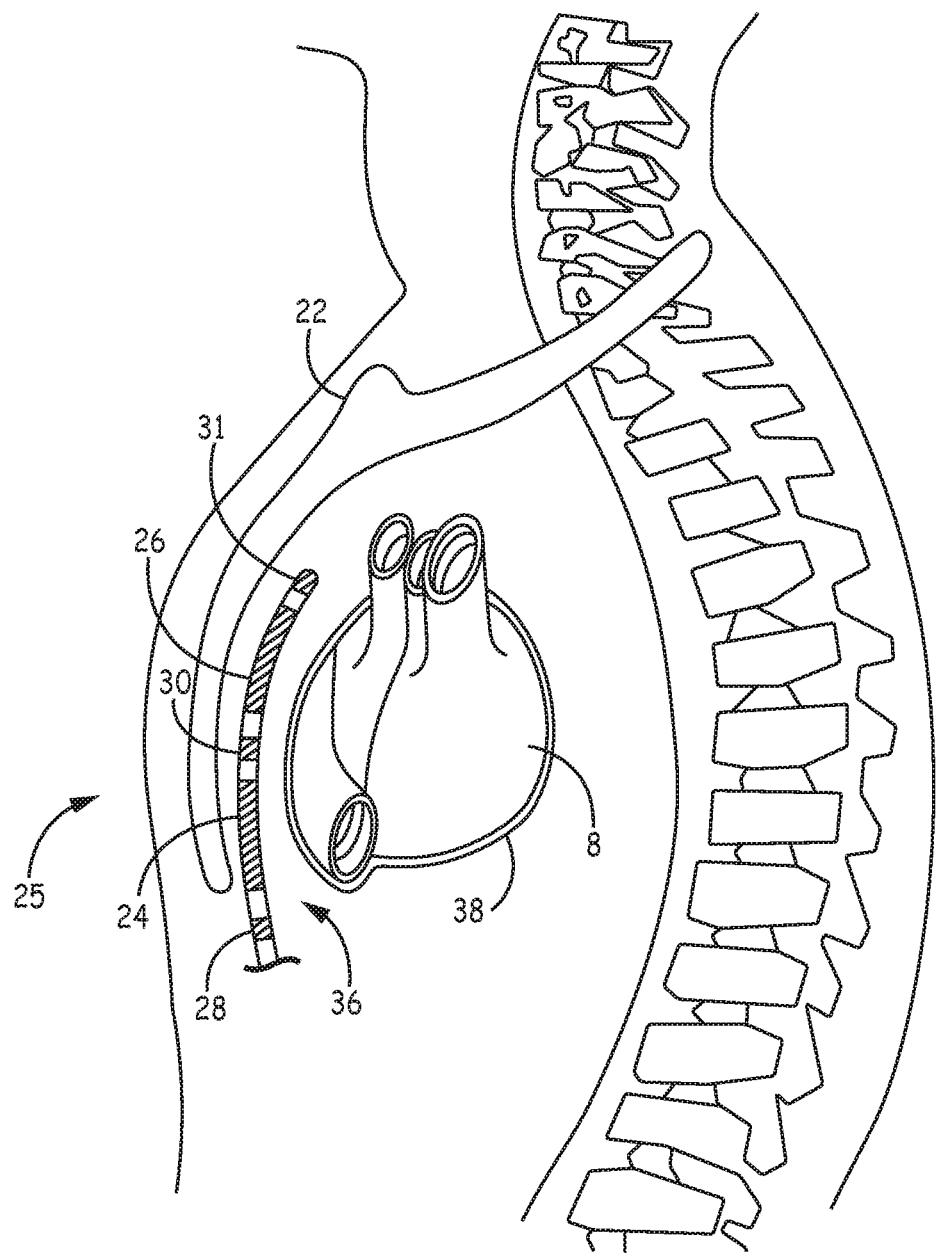
Figure 2C:
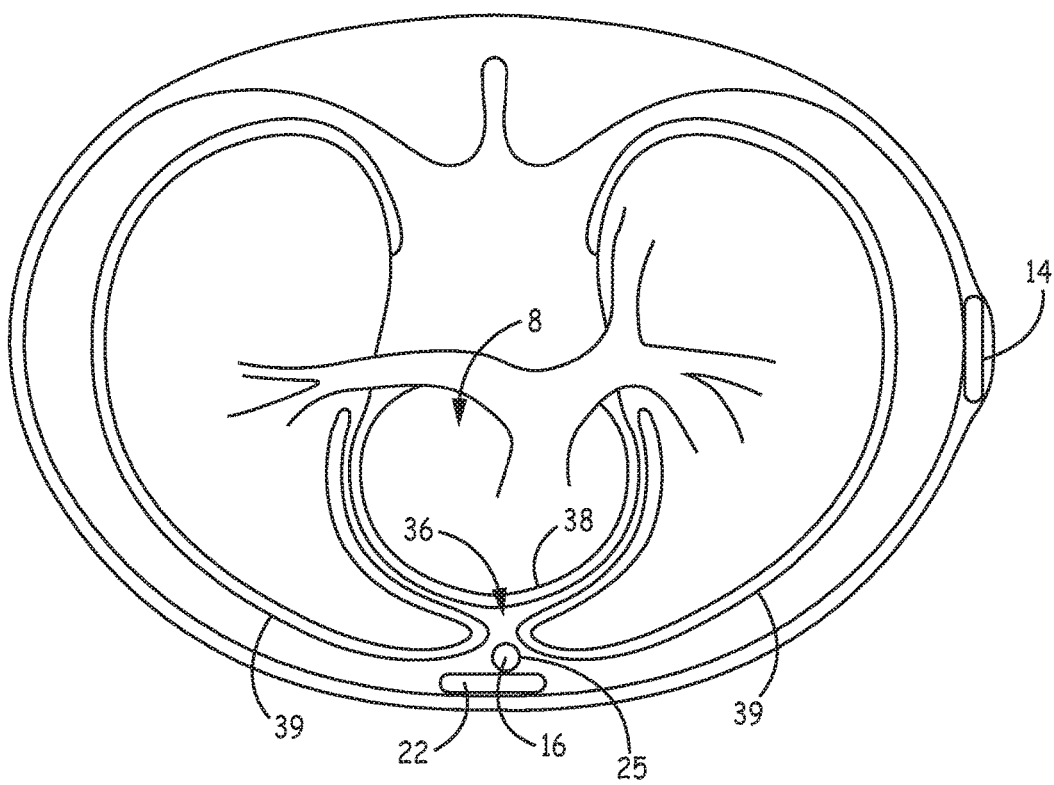

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the techniques described herein are generally disclosed in the above-incorporated patent applications.

Figure 3:
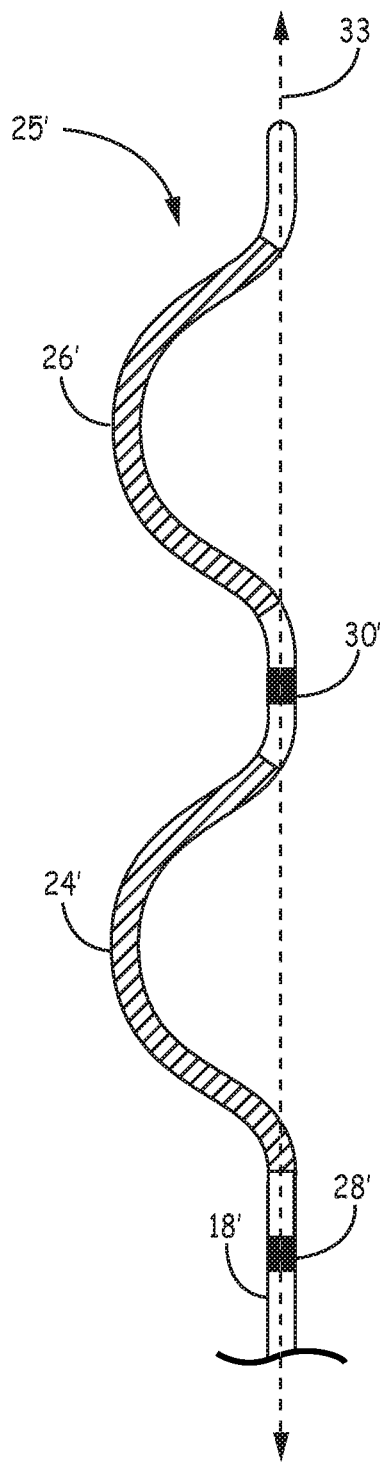
FIG. 3 is a conceptual diagram of a distal portion of an extra-cardiovascular lead having an electrode configuration according to another example.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. patent application Ser. No. 14/963,303, incorporated herein by reference in its entirety.

Figure 4:
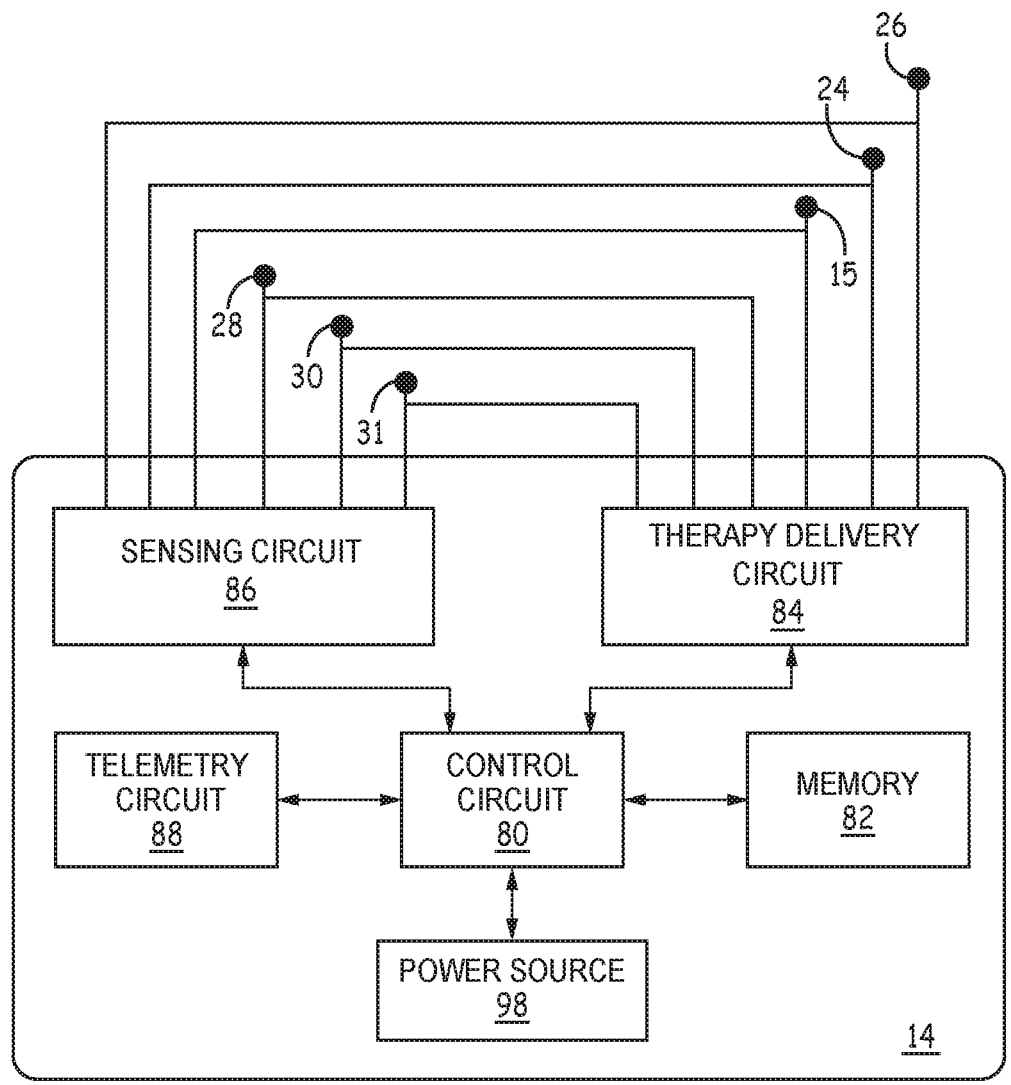
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor one or more cardiac electrical signals, determine when an electrical stimulation therapy is necessary, and deliver therapies as needed according to programmed therapy delivery algorithms and control parameters. The software, firmware and hardware are configured to detect ventricular tachyarrhythmia and may discriminate VT and VF for determining when ATP or CV/DF shocks are required. In some cases, ICD 14 may be configured to deliver bradycardia pacing when the heart rate falls below a programmed lower rate. ICD 14 is coupled to an extra-cardiovascular lead, such as lead 16 shown in FIG. 1A or lead 16' of FIG. 3, carrying extra-cardiovascular electrodes 24, 26, 28, 30 and 31 (if available), for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering cardiac pacing pulses, ATP and/or post-shock pacing pulses instead of low voltage capacitors.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components (e.g., circuits) is intended to highlight different functional aspects and does not necessarily imply that such components (e.g., circuits or modules) must be realized by separate hardware or software components. Rather, functionality associated with one or more components may be performed by separate hardware, firmware or software components, or integrated within common hardware, firmware or software components. For example, sensing operations may be performed by sensing circuit 86 under the control of control circuit 80 and identification of PWOS operations may be implemented in a processor of control circuit 80 executing instructions stored in memory 82.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, and 30 31 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 is enabled to selectively monitor one or more sensing vectors at a time selected from the available electrodes 24, 26, 28, 30, 31 and housing 15. For example, sensing circuit 86 may include switching circuitry for selecting which of electrodes 24, 26, 28, 30, 31 and housing 15 are coupled to sense amplifiers or other cardiac event detection circuitry included in one or more sensing channels of sensing circuit 86. Switching circuitry may include a switch array, switch matrix, multiplexer, or any other type of switching device suitable to selectively couple components of sensing circuit 86 to selected electrodes. In some instances, control circuit 80 may control the switching circuitry to selectively couple sensing circuit 86 to one or more sense electrode vectors. The cardiac event detection circuitry within sensing circuit 86 may include one or more sense amplifiers, filters, rectifiers, threshold detectors, comparators, analog-to-digital converters (ADCs), or other analog or digital components.

In some examples, sensing circuit 86 includes multiple sensing channels for acquiring cardiac electrical signals from multiple sensing vectors selected from electrodes 24, 26, 28, 30, 31 and housing 15. Each sensing channel may be configured to amplify, filter and rectify the cardiac electrical signal received from selected electrodes coupled to the respective sensing channel to improve the signal quality for sensing cardiac events, such as R-waves. For example, each sensing channel may include a pre-filter and amplifier for filtering and amplifying a signal received from a selected pair of electrodes. The resulting raw cardiac electrical signal may be passed from the pre-filter and amplifier to cardiac event detection circuitry for sensing cardiac events from the received cardiac electrical signal. Cardiac event detection circuitry may include a pre-filter and amplifier, an analog-to-digital converter, a bandpass filter, a rectifier, a sense amplifier and/or comparator for detecting a cardiac event when the cardiac electrical signal crosses a sensing threshold. For example, an R-wave sensing threshold may be automatically adjusted by sensing circuit 86 under the control of control circuit 80. The R-wave sensing threshold may have a starting threshold value set as a percentage of a maximum peak amplitude of the immediately preceding sensed R-wave. The R-wave sensing threshold may decrease from a starting value in a decaying or step-wise manner over predetermined time intervals. Parameters used to determine and control the R-wave sensing threshold values may be stored in memory 82 and controlled by hardware or firmware of control circuit 80 and/or sensing circuit 86. Some sensing threshold control parameters may be programmed by a user and passed from control circuit 80 to sensing circuit 86 via a data bus.

Sensing circuit 86 may sense R-waves according to a sensing threshold that is automatically adjusted. For example, the R-wave sensing threshold may decay from a starting percentage, e.g., 60% of the maximum peak amplitude of the most recently sensed R-wave. In other examples, the R-wave sensing threshold may be adjusted in a step-wise manner to multiple threshold levels at specified times after a sensing threshold crossing as disclosed in U.S. patent application Ser. No. 15/142,171 , incorporated herein by reference in its entirety.

Upon detecting a cardiac event based on a sensing threshold crossing, sensing circuit 86 may produce a sensed event signal, such as an R-wave sensed event signal, that is passed to control circuit 80. The sensed event signals are used by control circuit 80 for detecting cardiac rhythms and determining a need for therapy. Sensing circuit 86 may also pass a digitized cardiac electrical signal to control circuit 80 for waveform morphology analysis performed for detecting and discriminating heart rhythms.

Signals from the selected sensing vector may be passed through a bandpass filter and amplifier, provided to a multiplexer and converted to multi-bit digital signals by an analog-to-digital converter, all included in sensing circuit 86, for storage in random access memory included in memory 82 under control of a direct memory access circuit via a data/address bus. Control circuit 80 may be a microprocessor-based controller that employs digital signal analysis techniques to characterize the digitized signals stored in random access memory of memory 82 to recognize and classify the patient's heart rhythm employing any of numerous signal processing methodologies for analyzing cardiac signals and cardiac event waveforms, e.g., R-waves. Examples of algorithms that may be performed by ICD 14 for detecting, discriminating and treating tachyarrhythmia which may be adapted to include PWOS identification techniques described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

Therapy delivery circuit 84 includes charging circuitry; one or more charge storage devices, such as one or more high voltage capacitors and in some examples one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP or other cardiac pacing pulses are delivered.

For example, control circuit 80 may include pacer timing and control circuitry having programmable digital counters set by the microprocessor of the control circuit 80 for controlling the basic time intervals associated with various pacing modes or anti-tachycardia pacing sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within the pacer timing and control circuitry are reset upon sensing of R-waves as indicated by signals from sensing circuit 86. In accordance with the selected mode of pacing, pacing pulses are generated by a pulse output circuit of therapy delivery circuit 84 upon expiration of an escape interval counter. The pace output circuit is coupled to the desired electrodes via switch matrix for discharging one or more capacitors across the pacing load. The escape interval counters are reset upon generation of pacing pulses, and thereby control the basic timing of cardiac pacing functions, including anti-tachycardia pacing, bradycardia pacing, or post-shock pacing. The durations of the escape intervals are determined by control circuit 80 via a data/address bus. The value of the count present in the escape interval counters when reset by sensed R-waves can be used to measure RR intervals (RRIs) for detecting the occurrence of a variety of arrhythmias. An RRI is the time interval between two consecutively sensed R-waves.

As described below, control circuit 80 may monitor RRIs for detecting an RRI pattern that is evidence of PWOS. The pattern may be a pattern of alternating long and short RRIs, e.g., long-short-long-short, or clusters of sensed events occurring at short intervals separated by one long interval, e.g., short-short-long or short-short-short-long. When a pattern of RRIs that is indicative of PWOS is detected, e.g., when a predetermined number of sensed event clusters are detected based on RRI criteria, the waveforms of the digitized cardiac electrical signal corresponding to the RRI pattern of clustered sensed events may be analyzed by control circuit 80 for identifying PWOS. PWOS may be identified when RRI patterns and waveform morphology analysis meet PWOS detection criteria. If PWOS is identified, and a tachyarrhythmia is being detected, the tachyarrhythmia episode detection may be rejected or a scheduled tachyarrhythmia therapy may be canceled or withheld. If PWOS is identified, and a tachyarrhythmia is not being detected, analysis of sensed events, e.g., on a beat-by-beat basis, may be enabled to allow oversensed P-waves to be identified as they occur and ignored for the purposes of resetting pacing escape interval counters so that an oversensed P-wave does not inhibit pacing pulse delivery. Additionally or alternatively, if PWOS is identified, a cardiac signal segment may be stored and/or R-wave sensing control parameters may be adjusted to reduce the likelihood of PWOS in the future.

Memory 82 includes read-only memory (ROM) or other memory devices in which stored programs controlling the operation of the control circuit 80 reside. Memory 82 may further include random access memory (RAM) or flash memory configured as a number of recirculating buffers capable of holding a series of measured RRIs, cardiac signal segments, counts or other data for analysis by the control circuit 80 for predicting or diagnosing an arrhythmia.

In response to the detection of ventricular tachycardia, ATP may be delivered by loading a regimen from a microprocessor included in control circuit 80 into the pacer timing and control circuit according to the type and rate of tachycardia detected. In the event that the tachycardia is not terminated by ATP or if VF is detected and higher voltage cardioversion or defibrillation pulses are required, the control circuit activates cardioversion and defibrillation control circuitry included in control circuit 80 to initiate charging of the high voltage capacitors via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by the microprocessor of control circuit 80, a logic signal is generated on a capacitor full line passed to therapy delivery circuit 84, terminating charging. The defibrillation or cardioversion pulse is delivered to the heart under the control of the pacer timing and control circuitry by an output circuit of therapy delivery circuit 84 via a control bus. The output circuit, which may include multiple switches and may be in the form of an H-bridge circuit, determines the electrodes used for delivering the cardioversion or defibrillation pulse and the pulse wave shape. Therapy delivery charging and output circuitry and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5A:
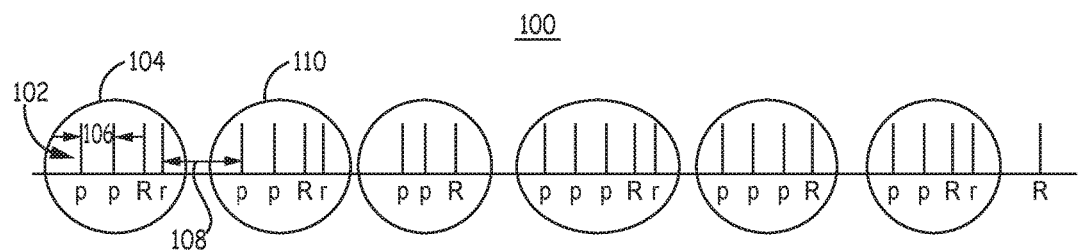
FIG. 5A is a conceptual diagram of R-wave sensed event signals that may be produced by the sensing circuit of the ICD of FIG. 1 during PWOS.

FIG. 5A is a conceptual diagram 100 of R-wave sensed event signals 102 that may be produced by sensing circuit 86 during PWOS. Events 102 are labeled as "P" for P-wave, "R" for R-wave and "r" designates a double-sensed R-wave in which an uppercase "R" immediately followed by a lowercase "r" represent sensed event signals produced by sensing the same QRS complex twice. When extra-cardiovascular electrodes are used to acquire a cardiac electrical signal, the QRS waveform may be relatively wide in some patient's compared to the QRS waveform of a signal received using transvenous, intracardiac electrodes or epicardial electrodes. As such, there may be a higher likelihood of double sensing an R-wave when a single R-wave signal exceeds the R-wave sensing threshold a second time outside of a blanking period.

The second time the R-wave is sensed the cardiac signal peak amplitude may be lower than the actual peak amplitude of the R-wave. When the R-wave sensing threshold is set as a percentage of the maximum R-wave amplitude, a decaying or decreasing R-wave sensing threshold starting at a relatively low amplitude may be crossed by a subsequent P-wave. In other cases, the R-wave sensed by extra-cardiovascular electrodes may be low in amplitude in some instances. Relatively small amplitude R-waves may still be larger than P-waves or T-waves and appropriately sensed as R-waves. However, when the starting R-wave sensing threshold is set as a percentage of the maximum peak amplitude of a sensed R-wave, the starting threshold may be set relatively low when the R-wave peak amplitude is low. A P-wave may be oversensed following the low-amplitude R-wave in some instances, particularly when the heart rate is low.

Figure 5B:
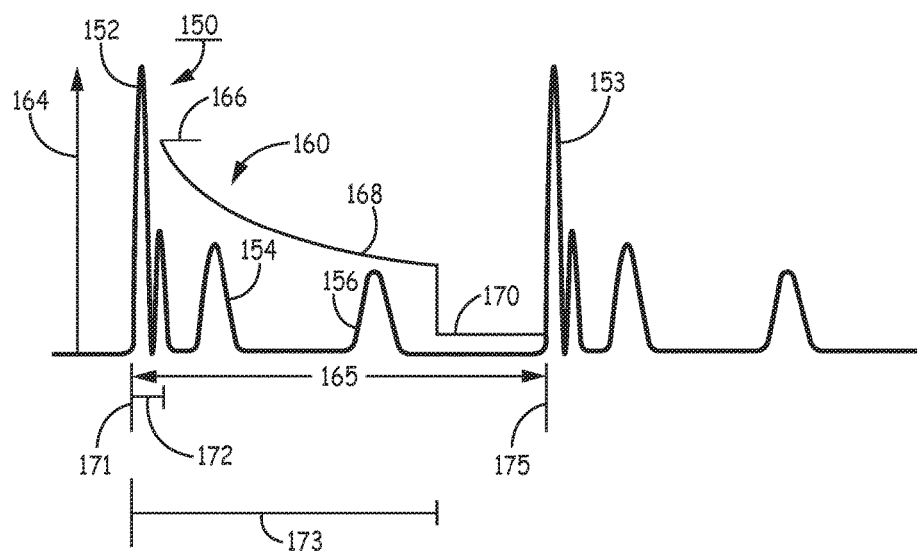
FIG. 5B is a conceptual diagram of a bandpass filtered and rectified cardiac electrical signal depicting cardiac events and an R-wave sensing threshold.

FIG. 5B is a conceptual diagram of a bandpass filtered and rectified cardiac electrical signal 150 including R-wave 152 followed by a T-wave 154 and P-wave 156, with no PWOS. The R-wave sensing threshold 160 is set to a starting threshold value 166 following a blanking period 172 after R-wave 152 is sensed. R-wave 152 is sensed at time 171 and blanking period 172 is started.

During blanking period 172, the maximum peak amplitude 164 of R-wave 152 is determined and used to set starting R-wave sensing threshold value 166, e.g., approximately 60% of the maximum peak amplitude 164. R-wave sensing threshold 160 decreases over time from the starting value 166. In the example shown, R-wave sensing threshold 160 is shown to decrease according to a predetermined decay rate 168 from the starting value 166 up to the expiration of a predetermined time interval 173, or until a minimum sensing threshold value 170 is reached, whichever occurs first. If time interval 173 expires, the R-wave sensing threshold 160 drops to the minimum sensing threshold value 170, which may be equal to a programmed sensitivity setting. In other examples, R-wave sensing threshold 160 may decrease linearly and/or according to one or more step-wise drops or according to other R-wave sensing threshold control parameters, including the multi-level R-wave sensing threshold examples disclosed in the above-incorporated U.S. patent application Ser. No. 15/142,171.

When the R-wave amplitude 164 is relatively high, the starting value 166 based on amplitude 164 is relatively high such that the decaying R-wave sensing threshold 160 remains greater than the amplitude of P-wave 156 (and T-wave 154) such that PWOS does not occur. The next R-wave 153 is sensed at time 175 when the cardiac electrical signal crosses the R-wave sensing threshold 160, which has been reduced to the minimum value 170. The time interval 165 is determined as the RRI between consecutively sensed R-waves 152 and 153 and may be used by control circuit 80 in detecting patterns of PWOS. For example, RRI 165 may represent a long RRI in an analysis of RRIs performed for detecting a pattern including long and short RRIs that may be evidence of PWOS.

Figure 5C:
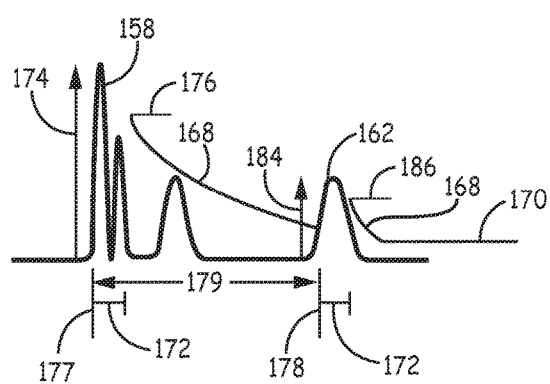
FIG. 5C is a conceptual diagram of a bandpass filtered and rectified cardiac electrical signal showing an example of PWOS when the R-wave amplitude is relatively small.

In FIG. 5C, R-wave 158 is followed by a T-wave and an oversensed P-wave 162. When a relatively small amplitude R-wave 158 occurs, or the ratio of the R-wave amplitude 174 to the P-wave amplitude 184 is relatively small, the starting R-wave sensing threshold 176 based on R-wave maximum peak amplitude 174 is relatively low compared to the P-wave maximum peak amplitude 184. As R-wave sensing threshold decreases from the starting value 176 according to decay rate 168, it falls below the amplitude 184 of P-wave 162. P-wave 162 is oversensed at time 178, causing sensing circuit 86 to produce a false R-wave sensed event signal. The R-wave sensing threshold 160 is set to a starting value 186 based on the peak amplitude 184 of P-wave 162, falsely detected as an R-wave, resulting in the R-wave sensing threshold returning to the minimum sensing threshold 170 quickly as it decreases at decay rate 168.

The time interval 179 between the R-wave 158 sensed at time 177 and the P-wave 162 sensed at time 178 is determined as an RRI, but is a relatively short RRI and may be identified by control circuit 80 in a pattern of RRIs that is evidence of PWOS. In the presence of an atrial tachyarrhythmia, such as atrial fibrillation or atrial flutter, multiple P-waves may occur between R-waves. When P-wave 162 is oversensed and is followed by a relatively low R-wave sensing threshold that is based on the low peak amplitude 184 of P-wave 162, multiple P-waves may be oversensed sequentially leading to a cluster of sensed events occurring at short intervals.

As shown by FIG. 5C, when a relatively small amplitude R-wave 158 occurs, subsequent PWOS may occur, particularly when the R-wave sensing threshold starting value is set based on the maximum peak amplitude of the most recent sensed event. PWOS may occur repetitively until a relatively larger amplitude R-wave is sensed, which resets the R-wave sensing threshold to a proportionally higher starting value. The higher starting value may maintain the R-wave sensing threshold above the P-wave amplitude and interrupt the sequence of sensed events that include PWOS.

Relatively small R-waves may occur during a normal or fast ventricular rate, leading to PWOS and an overestimation of the ventricular rate. VT or VF may be falsely detected resulting in an unneeded therapy, such as an unnecessary cardioversion/defibrillation shock. Small R-waves may also occur during a slow ventricular rate leading to PWOS and an overestimation of the ventricular rate when the patient may be experiencing bradycardia. In this case, appropriate bradycardia pacing may be withheld due to the PWOS because R-wave sensed event signals cause the pacing escape interval to be reset prior to expiration and pacing pulse delivery. As such, PWOS may lead to false detection of ventricular tachyarrhythmia and unnecessary therapy, and PWOS may lead to missed detection of bradycardia intervals and withholding of an appropriate bradycardia pacing therapy.

Figure 6:
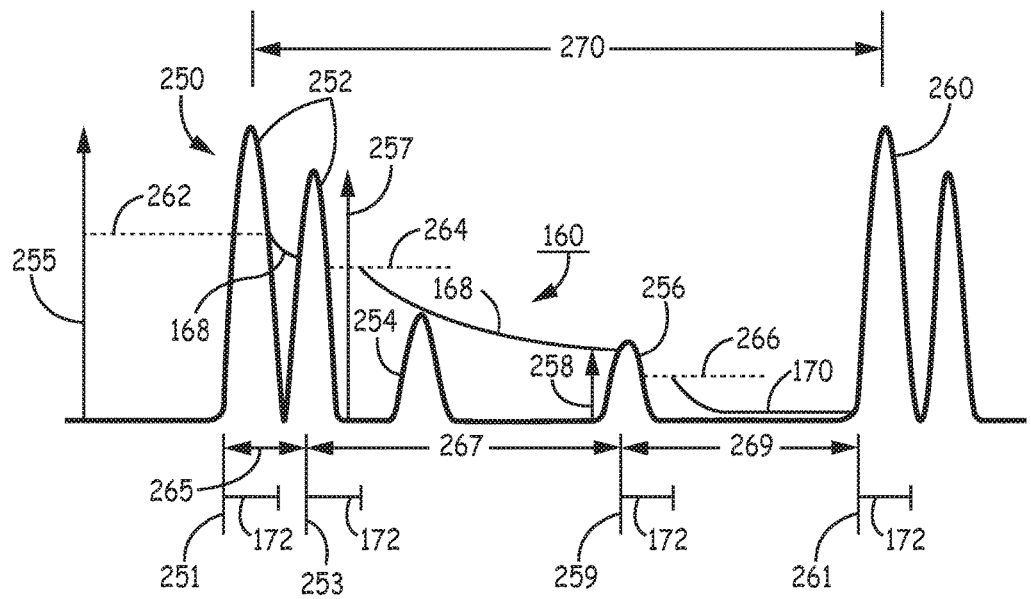
FIG. 6 is a conceptual diagram of a bandpass filtered and rectified cardiac electrical signal showing another example of PWOS.

FIG. 6 is a conceptual diagram of a bandpass filtered and rectified cardiac electrical signal 250 including R-waves 252 and 260 with intervening T-wave 254 and P-wave 256. In this example, double sensing of R-wave 252 and oversensing of P-wave 256 occur resulting in a cluster of sensed events at times 251, 253, 259 and 261 occurring at relatively short RRIs 265, 267, and 269, respectively.

R-wave 252 is sensed first at time 251, and blanking period 172 is started. The R-wave sensing threshold 160 is set to a starting threshold value 262 following blanking period 172. R-wave sensing threshold 160 decays at decay rate 168. R-wave 252 has a relatively wide signal width in this example such that when the first blanking interval 172 started at time 251 expires, the rectified R-wave 252 crosses the R-wave sensing threshold 160 a second time at time 253 outside blanking interval 172, starting another blanking interval 172. Control circuit 80 determines an RRI 265 between R-wave sensed event signals received at time 251 and time 253.

The R-wave sensing threshold 160 is set to a starting value 264 based on a percentage of the maximum peak amplitude 257 detected during the blanking interval 172 started at time 253 corresponding to the second time R-wave 252 is sensed. The starting value 264 of R-wave sensing threshold 160 is lower than the starting threshold 262 that is based on a percentage of the true maximum peak amplitude 255 of R-wave 252. R-wave sensing threshold 160 may decrease at decay rate 168 or another linear or step-wise decreasing manner. P-wave 256 crosses R-wave sensing threshold 160 at time 259, starting a new blanking interval 172. Control circuit 80 determines RRI 267 as the time interval between the R-wave sensed event signals received at time 253 and time 259.

After the blanking interval 172 is started upon sensing P-wave 256 at time 259, the R-wave sensing threshold is set to a starting value 266 based on a percentage of the maximum peak amplitude 258 of P-wave 256. The R-wave sensing threshold decreases at a decay rate 168 until it reaches a minimum sensing threshold value 170, e.g., the programmed sensitivity setting. R-wave 260 is sensed at time 261 when the cardiac electrical signal 250 crosses R-wave sensing threshold 160. Control circuit 80 determines the next RRI 269 as the time interval between R-wave sensed event signals received from sensing circuit 86 at time 259 and at time 261.

All of these RRIs 265, 267, and 269 are relatively short compared to a true RRI 270 between consecutive R-waves 252 and 260. This cluster of R-wave sensed events at times 251, 253, 259 and 261 defining relatively short RRIs may be identified and detected as evidence of PWOS by control circuit 80. Additional analysis of the sensed events, double sensing of R-wave 252, P-wave 256 and R-wave 260 in this example, may be performed in response to detecting the cluster of sensed events, e.g., as described in conjunction with FIG. 8.

Figure 7:
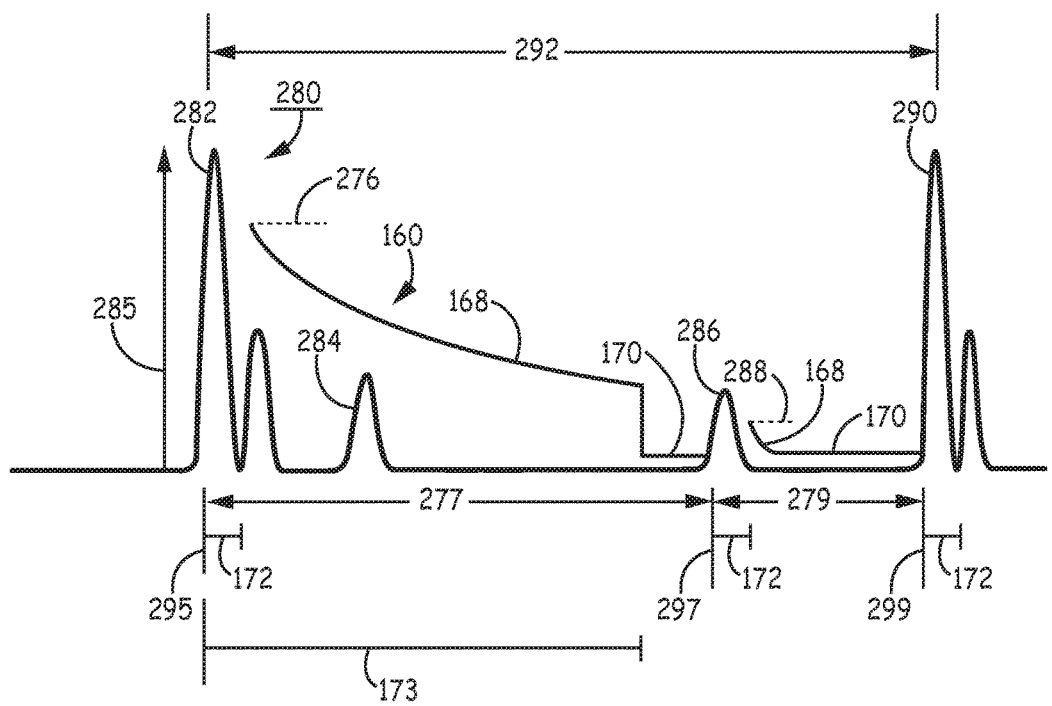
FIG. 7 is a conceptual diagram of a bandpass filtered and rectified cardiac electrical signal showing yet another example of PWOS.

FIG. 7 is a conceptual diagram of a bandpass filtered and rectified cardiac electrical signal 280 including R-waves 282 and 290 with intervening T-wave 284 and P-wave 286. In this example, the heart rate is very slow, e.g., less than 60 beats per minute or even slower at less than 40 beats per minute. R-wave 282 is properly sensed at time 295 when the cardiac electrical signal 280 crosses R-wave sensing threshold 160. After the blanking interval 172, R-wave sensing threshold 160 is set to a starting value 276 based on a percentage of the maximum peak amplitude 285 of R-wave 282. R-wave sensing threshold 160 decreases at decay rate 168 and is adjusted to the minimum sensing threshold value 170 after the pre-determined drop time interval 173. The drop time interval may be, for example, 1.5 seconds or 2 seconds in some examples. Because the heart rate is very slow in this example, P-wave 286 occurs after the drop time interval 173 expires, and cardiac electrical signal 280 crosses the R-wave sensing threshold 160 set to the minimum value 170.

P-wave 286 is sensed at time 297, starting a new blanking period 172. The R-wave sensing threshold 160 is adjusted to a starting value 288 based on the peak amplitude of P-wave 286 and decays to the minimum threshold value 170. R-wave 290 is sensed at time 299 when the cardiac electrical signal 270 cross the R-wave sensing threshold 160. Control circuit 80 determines RRI 277 between R-wave sensed event signals received from sensing circuit 86 at times 295 and 297 and determines RRI 279 between R-wave sensed event signals received at times 297 and 299. These RRIs 277 and 279 are each shorter than the true RRI 292. The true RRI 292 may be longer than a programmed lower pacing rate interval. For example, a lower pacing rate interval may be programmed to be 1.0 seconds for a pacing rate of 60 pulses per minute or 1.5 seconds for a pacing rate of 40 pulses per minute. If the RRI 277 is shorter than the programmed lower rate interval, a pacing escape interval started at time 295, when R-wave 282 is sensed, may be reset at time 297 in response to an R-wave sensed event signal at time 297. PWOS may occur during a slow heart rate and lead to inhibition of pacing pulses when the true heart rate is slower than the rate corresponding to the programmed lower rate interval.

Returning to FIG. 5A, sensed event clusters 104 may include multiple events sensed at relatively short RRIs 106 due to PWOS. Each vertical line represents an event sensed as an R-wave by sensing circuit 86, resulting in an R-wave sensed event signal passed to control circuit 80. As such the intervals between the consecutively sensed events, such as interval 106 and interval 108 are measured as RRIs by control circuit 80 as the time interval between consecutively received R-wave sensed event signals. In this example, multiple P-waves are oversensed for each R-wave due to an atrial tachyarrhythmia, with or without some degree of atrioventricular conduction block. The degree of AV conduction block, (e.g., no AV conduction block, first degree, second degree, or third degree complete AV conduction block) affects how many P-waves are conducted to the ventricles and therefore affects how many P-waves occur during one RR interval and the regularity of the P-R intervals during an atrial tachyarrhythmia. Each sensed event cluster 104 is separated from the next consecutive cluster 110 by a relatively long RRI 108. Control circuit 80 may apply PWOS detection criteria to R-wave sensed event signals and cardiac electrical signal waveforms occurring during sensed event clusters to detect PWOS as described herein, e.g., in conjunction with FIGS. 8-14.

Depending on multiple factors, as illustrated by the examples of FIG. 5C, FIG. 6 and FIG. 7, such as the intrinsic ventricular rate, R-wave amplitude, P-wave amplitude, underlying AV conduction, and intrinsic atrial rhythm (e.g., presence of an atrial arrhythmia such as atrial flutter, atrial fibrillation, atrial tachyarrhythmia, etc.), the number of P-waves oversensed in each sensed event cluster 104, 110, etc., and the relative RRIs during and between clusters, may vary. Cluster detection criteria for detecting clusters of sensed events and identifying PWOS may be established according to the cluster patterns observed or expected in an individual patient based on their particular rhythm history and cardiac electrical signal characteristics. While FIG. 5A depicts the RRI pattern during PWOS as multiple sensed event clusters separated by relatively longer RRIs, in other cases PWOS may result in alternating long and short RRIs, e.g., in the example of FIG. 7 during a slow heart rate when a single P-wave 286 is oversensed during each true RRI 292.

Figure 8:
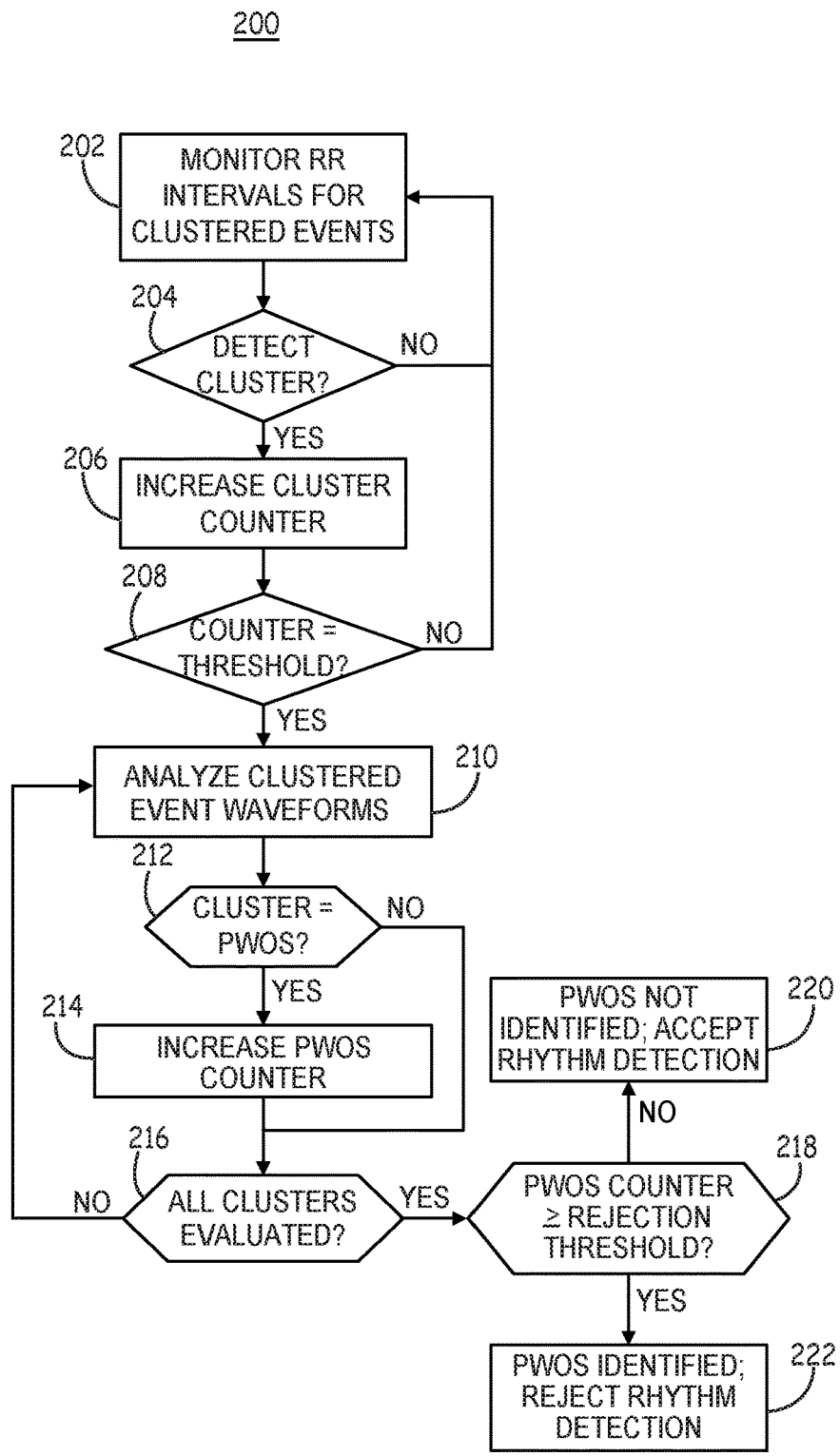
FIG. 8 is a flow chart of a method for identifying and responding to PWOS according to one example.

FIG. 8 is a flow chart 200 of a method for identifying and responding to PWOS according to one example. At block 202, control circuit 80 monitors RRIs for clustered sensed events. One method for detecting a cluster of sensed events is described in conjunction with FIG. 7. Briefly, RRIs are determined, e.g., based on the time or count that an escape interval timer has reached upon being reset due to the control circuit 80 receiving an R-wave sensed event signal from sensing circuit 86. Long and short RRI thresholds may be applied to consecutively determined RRIs for detecting a pattern of clustered sensed events. As shown in FIG. 5A, a pattern of clustered sensed events may include two or more short RRIs 106 followed by a long RRI 108. In other examples, PWOS may be characterized by S-L-S-L intervals when a single P-wave is oversensed during each true RRI. This may occur during a slow heart rate, when R-wave amplitude is low and AV conduction is intact. As such, in some examples, a cluster of sensed events may include as few as two sensed events separated by a short RRI from each other and separated from other clusters of sensed events by one long RRI. In other examples, a cluster of sensed events may include 3, 4, 5 or more sensed events separated by short RRIs. Multiple short RRIs within a cluster may vary from each other but are all less than a short RRI threshold. The clustered sensed events may include at least one P-wave and will typically include at least one P-R or R-P interval as shown in the examples of FIGS. 5C, 6, and 7. The clustered sensed events may include a double-sensed R-wave, multiple oversensed P-waves, and oversensed T-waves in other examples.

If a cluster is detected based on cluster detection criteria, as determined at block 204, control circuit 80 may increase a cluster counter at block 206. The cluster counter may be compared to a threshold at block 208. If the counter reaches a predetermined number of sensed event clusters, e.g., 3, 4, 5 or other threshold number of clusters, the waveforms of sensed events of each cluster are analyzed by control circuit 80 at block 210. Based on the waveform analysis, the cluster is either identified or not identified as PWOS. The waveform analysis may include event amplitude analysis, waveform morphology analysis, waveform slope analysis or other analysis of the event waveforms. One example of the analysis performed at block 210 is described below in conjunction with FIG. 8.

If PWOS is not identified, and all of the predetermined number of clusters have not been identified, "no" branch of block 216, control circuit 80 analyzes the next cluster by returning to block 210. If the cluster is confirmed to be PWOS, "yes" branch of block 212, a PWOS counter may be increased at block 214 by control circuit 80. Once all of the predetermined number of clusters have been evaluated, "yes" branch of block 216, the PWOS count adjusted at block 214 is compared to a PWOS rejection threshold at block 218. If the PWOS counter does not reach a rhythm rejection threshold, PWOS is not identified as indicated at block 220. The heart rhythm being sensed or detected by the ICD is deemed valid. For example, if VT or VF is being detected, the rhythm detection is acceptable and a therapy may be delivered according to programmed tachyarrhythmia therapies. If VT or VF is not being detected and RRIs less than a programmed bradycardia lower pacing rate interval are being determined, the RRIs are deemed correct. No bradycardia therapy is required.

If the number of clusters confirmed to be PWOS does reach the rejection threshold at block 218, PWOS is identified, and the currently sensed heart rhythm is rejected at block 222. If a VT or VF episode is being detected, the VT or VF detection may be rejected at block 222 or a ventricular tachyarrhythmia therapy is withheld. If normal sinus rhythm is being sensed, e.g., if RRIs are being determined that are less than a bradycardia lower pacing rate interval, with no bradycardia pacing being delivered, the sensed rhythm is rejected. ICD 14 may adjust therapy control parameters by enabling monitoring of event amplitudes, e.g., as described in conjunction with FIG. 13, or other corrective actions may be taken to identify oversensed P-waves as they occur so that they may be ignored for the purposes of controlling ventricular pacing escape interval timers and ventricular pacing pulse delivery. Examples of a PWOS-based rhythm rejection response are described in conjunction with FIG. 11.

Figure 9:
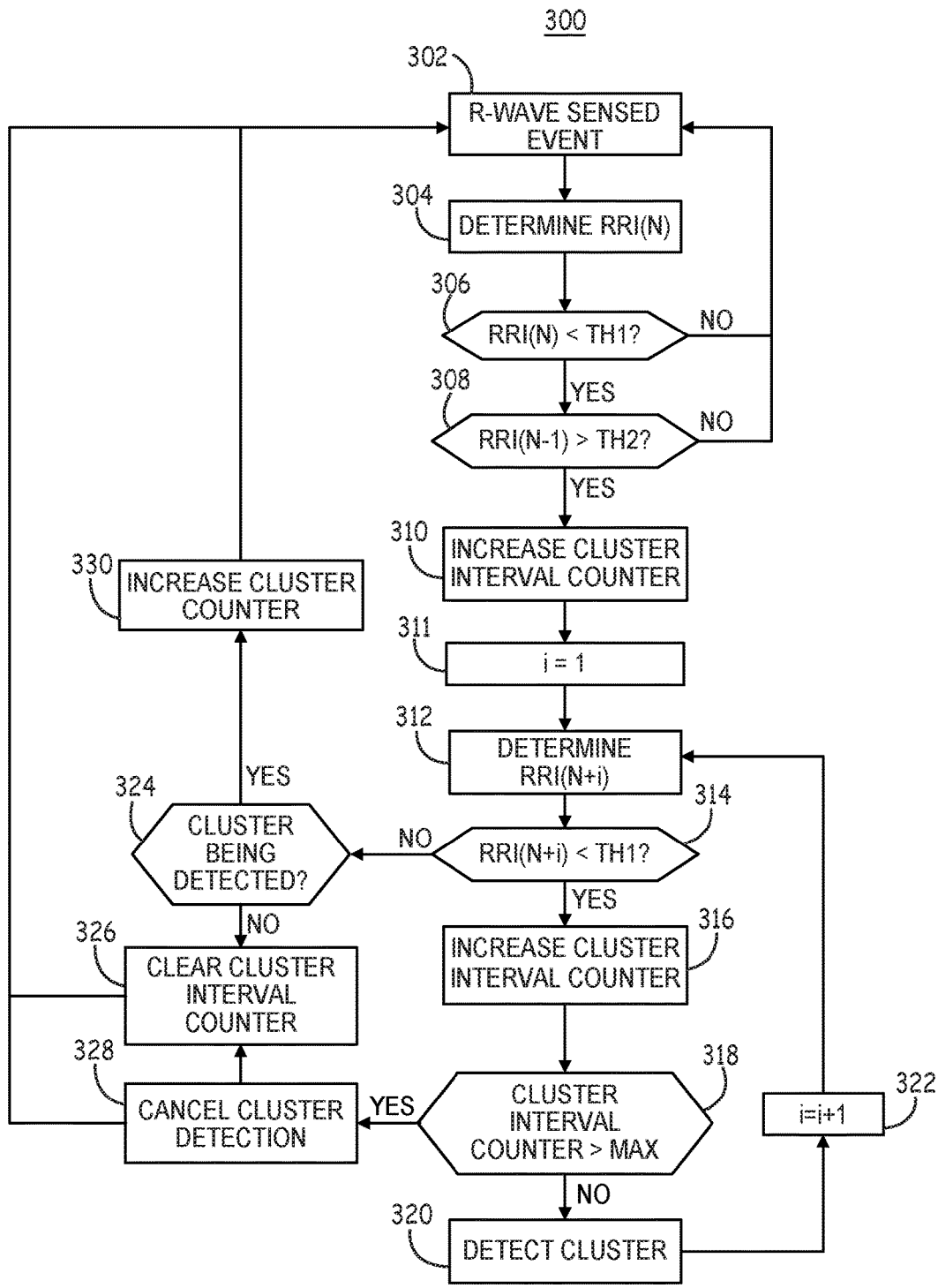
FIG. 9 is a flow chart of a method performed by the ICD of FIG. 1A for detecting a sensed event cluster according to one example.
Figure 10:
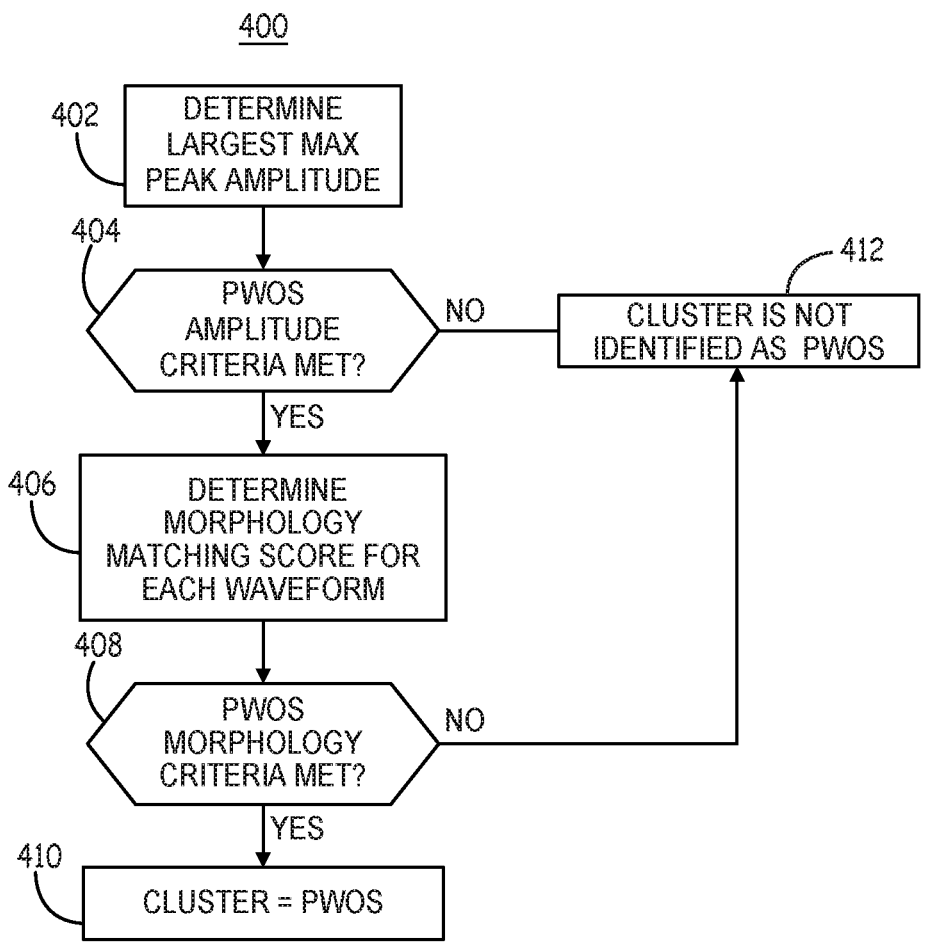
FIG. 10 is a flow chart of a method for analyzing clustered event waveforms for identifying a sensed event cluster as PWOS.

FIG. 9 is a flow chart 300 of a method that may be performed by ICD 14 for detecting a sensed event cluster according to one example. The method of flow chart 300 may correspond to blocks 202, 204 and 206 of FIG. 8 where RRIs are monitored for detecting a sensed event cluster and a cluster counter is increased when a cluster is detected. At block 302, control circuit 80 receives an R-wave sensed event signal from sensing circuit 86. This sensed event signal is referred to as an "R-wave sensed event signal," because it is a signal produced in response to the cardiac electrical signal crossing the R-wave sensing threshold. The actual event crossing the R-wave sensing threshold, however, may correspond to an R-wave, a P-wave, or even a T-wave or other non-cardiac electrical noise, and thus may be a false R-wave sensed event signal.

At block 304, control circuit 80 determines RRI(N) as the time interval ending with the currently received R-wave sensed event signal and beginning with the most recent preceding R-wave sensed event signal. This RRI(N) is compared to a short interval threshold (TH1) at block 306. The short interval threshold TH1 may be set to a fixed interval, for example approximately 210 ms, 200 ms, 190 ms, 180 ms, 150 ms, or other predetermined time interval, which may be based on a normally expected P-R interval for the patient. The P-R interval, e.g., the time interval from a sensed P-wave or its maximum peak amplitude to the next sensed R-wave or its maximum peak amplitude, may be determined automatically by ICD 14 or measured by a clinician. The short interval threshold TH1 may be automatically set or programmed to be slightly greater than the expected P-R interval for the patient.

In some examples, RRI(N) (and subsequent RRIs) may be compared to an interval range. When non-cardiac noise is present, such as electromagnetic interference, very short RRIs may occur when the non-cardiac noise is falsely sensed as R-waves. Accordingly, criteria for identifying PWOS may include a minimum RRI threshold as well as a maximum RRI threshold for identifying short intervals between R-wave sensed event signals that may be caused by PWOS. The minimum RRI threshold may correspond to a minimum expected P-R interval and the maximum RRI may correspond to a maximum expected P-R interval. A normal P-R interval range may be approximately 120 ms to 200 ms. This range may be adjusted up or down or widened or narrowed based on individual patient need.

If RRI(N) is not less than the short interval threshold, control circuit 80 returns to block 302 to wait for the next R-wave sensed event signal. The RRI(N) is stored in memory 82, however, for use in evaluating a series of RRIs. For example, a series of up to 3, 4, 6, or more consecutive RRIs needed for detecting a cluster pattern according to cluster detection criteria may be stored in memory 82 in a circulating buffer.

If RRI(N) is less than the short interval threshold at block 306, the most recent preceding RRI, RRI(N−1) may be compared to a long interval threshold (TH2) at block 308. The long interval threshold TH2 may be set to a minimum expected R-P interval when the heart rate is below a tachyarrhythmia rate. For example, the long interval threshold TH2 may be set to approximately 250 ms, 300 ms, 350 ms, 400 ms or other predetermined time interval. A short RRI preceded by a long RRI may be the onset of a cluster of sensed events. If the preceding interval is not longer than the long interval threshold, the control circuit 80 waits for the next R-wave sensed event signal at block 302. If the preceding RRI(N−1) is longer than the long interval threshold, the events defining the beginning and end of RRI(N) may be clustered events. A cluster interval counter is set to one at block 310 to begin counting the number of RRIs following the longer RRI(N−1) that are less than the short interval threshold.

At block 312, control circuit 80 determines the next RRI, RRI(N+i) where i is initially set to 1 at block 311. The next RRI(N+1) is compared to the short interval threshold at block 314. If the comparison at block 314 is true, the cluster interval counter is again increased at block 316. The cluster interval counter is compared to a maximum number of short intervals at block 318. If a maximum number of intervals has not been reached, but the cluster interval counter has been increased, a cluster is being detected at bock 320. In this example, if at least two consecutive short intervals follow a long interval based on the short and long interval thresholds or ranges, a sensed event cluster is being detected. In other examples, the cluster interval counter may be compared to a cluster detection threshold that requires a predetermined number of short intervals in order to detect a cluster. In some cases, as few as one short interval (preceded and followed by a long interval) may be detected as a cluster of sensed events. In other examples, at least two or at least three short intervals may be required to detect a sensed event cluster such that at least three sensed events or at least four sensed events are clustered together at short intervals.

The cluster interval counter is compared to a maximum limit at block 318 so that events occurring at a sustained fast rate are not detected as a very long cluster, leading to PWOS detection. Events occurring at a sustained fast rate may be a true ventricular tachyarrhythmia. When the cluster interval counter exceeds a maximum number of short intervals, therefore, the cluster detection may be cancelled at block 328. The cluster interval counter is cleared at block 326 and the control circuit 80 returns to block 302 to repeat the process beginning with the next R-wave.

If a cluster is being detected (block 320), i is increased by one at block 322, where i is used to identify the next RRI(N+i) interval. The RRI(N+i) is determined at block 312 and compared to the short interval threshold at block 314. If RRI(N+i) is not less than the short interval threshold, and a cluster is being detected based on one or more preceding short RRIs, as determined at block 324, a cluster counter is increased by one at block 330. If a cluster is not being detected, for example if the cluster interval counter has not been increased a required number of times based on comparisons of the RRIs to the short interval threshold or range, the cluster interval counter is cleared at block 326. A sensed event cluster is not detected and the cluster interval counter is not increased. Control circuit 80 returns to block 302 to continue monitoring RRIs.

If the cluster counter is increased at block 330, the cluster counter may be compared to a counter threshold at block 208 of flow chart 200 (FIG. 6) as described previously. Once a threshold number of sensed event clusters are identified based on RRIs, the clustered event waveforms may be analyzed at block 210 for identifying PWOS. In some examples, as few as one cluster of two sensed events occurring at one short RRI preceded and followed by long RRIs, based on the long and short RRI thresholds or ranges, may result in a cluster being detected and the cluster counter reaching a counter threshold at block 208 to cause control circuit 80 to perform further analysis for identifying PWOS at block 210.

FIG. 8 is a flow chart 400 of one method for analyzing the clustered event waveforms at block 210 of FIG. 6 for identifying a sensed event cluster as PWOS at block 212. After the cluster counter reaches a threshold number of clusters, e.g., 1, 2, 3, 4, 5 or other predetermined number of clusters, analysis of the event waveforms of each cluster begins at block 402. The control circuit 80 may receive a digitized, filtered and rectified cardiac electrical from sensing circuit 86 that is buffered in memory 82 in a circulating buffer to be available for waveform analysis if the cluster counter reaches the threshold.

Each cluster may be defined to start on the first R-wave sensed event signal defining the beginning of the first short RRI(N) that is less than the short interval threshold (and defines the end of the immediately preceding long RRI(N-1) that is greater than the long interval threshold). The sensed event cluster may also be defined to end on the last R-wave sensed event signal that defines the first RRI(N+i) that is not less than the short interval threshold after the cluster interval counter begins counting short RRIs. Alternatively, the sensed event cluster may end on the preceding sensed event that defines the beginning of the last short RRI. The last R-wave that defines the end of the last short RRI and the start of the first long RRI after one or more short RRIs may be an R-wave as shown in FIG. 5A.

In one example, the maximum peak amplitude for each sensed event of a given cluster, including the starting and ending events, may be determined during a blanking interval following an R-wave sensing threshold crossing. The maximum peak amplitude may be stored in memory 82 in a circulating buffer with the timing of the corresponding R-wave sensed event signal. When the cluster counter reaches the threshold, control circuit 80 may determine the largest maximum peak amplitude stored for each respective R-wave sensed event during a given cluster at block 402. Alternatively the largest maximum peak amplitude out of all events during the cluster may be determined from the buffered, digitized cardiac electrical signal.

The largest maximum peak amplitude for the sensed event cluster is compared to an amplitude threshold at block 404. In some patients, PWOS may be most likely to occur when a relatively small amplitude R-wave occurs causing the R-wave sensing threshold starting value to be set to a relatively low amplitude as illustrated in FIG. 5C. As such, one criterion for identifying a cluster of sensed events as PWOS may be that the largest maximum peak amplitude be less than a threshold amplitude, indicating that if the cluster of events includes a true R-wave, it is a small amplitude R-wave and otherwise all of the sensed events have an amplitude that is not greater than an expected P-wave amplitude. The amplitude threshold may be approximately 200 millivolts or set based on determining a baseline P-wave and R-wave amplitude.

Amplitude criteria for identifying PWOS may require that the largest maximum peak amplitude of all sensed events of a cluster be less than the amplitude threshold at block 404. In other examples, a percentage or portion of all sensed events of a cluster may be required to be less than the amplitude threshold. For example, if a cluster includes four sensed events, three out of the four events may be required to have a maximum amplitude less than the amplitude threshold. A normal R-wave may be sensed during a sequence of oversensed P-waves as shown in FIG. 5A, e.g., when an atrial arrhythmia is occurring and the ventricular rate is slow and/or R-wave amplitude to P-wave amplitude ratio is relatively small. As such, amplitude criteria for detecting PWOS may allow for one or more large amplitude sensed events to occur as long as a predetermined percentage or portion of the sensed event waveforms have a maximum amplitude that is less than the amplitude threshold.

In other examples, the last sensed event of an event cluster may be excluded from comparison to an amplitude threshold at block 404. A relatively large amplitude R-wave may reset the starting R-wave sensing threshold value to a relatively high value that precludes PWOS on the next beat. The last sensed event of an event cluster that starts the RRI that is greater than the short interval threshold, concluding the series of short RRIs, may be a true R-wave. As long as all, or at least a predetermined portion, of the sensed events prior to the last sensed event of the cluster are less than the amplitude threshold, the cluster of sensed events may satisfy amplitude criteria required for identifying PWOS at block 404.

If the amplitude criteria for identifying PWOS are not satisfied at block 404, the cluster is not identified as PWOS at block 412. If the amplitude criteria are met, additional waveform morphology analysis may be performed at block 406. In one example, a morphology matching score is determined for each sensed event waveform of the cluster by comparing the waveform to a known R-wave template. An R-wave template may be previously generated and stored in memory 82, e.g., by aligning and averaging multiple R-wave signals acquired during normal sinus rhythm. The waveform of each sensed event may be aligned with the R-wave template and the differences between each aligned pair of sample points may be determined for determining a morphology match score for each waveform. Various morphology matching algorithms may be used, including wavelet transform or other transform methods. Examples of methods for generating an R-wave template and determining a morphology matching score are generally disclosed in U.S. Pat. No. 6,393,316 (Gillberg, et al.), U.S. Pat. No. 8,825,145 (Zhang et al.), U.S. Pat. No. 8,965,505 (Charlton, et al.), and U.S. Pat. No. 8,983,586 (Zhang et al.), all of which are incorporated herein by reference in their entirety.

At block 408, control circuit 80 determines if morphology criteria for identifying PWOS are met. In one example, the morphology matching scores for each event of the cluster determined at block 406 are compared to a match threshold. As long as all or a predetermined percentage or number of all of the sensed event waveforms of the cluster have a matching score that is less than the match threshold, the PWOS morphology criteria are met at block 408. A low matching score indicates a relatively poor correlation between the sensed event waveforms and the R-wave template, indicating that the waveforms sensed as R-waves are unlikely to be true R-waves. For example, if the morphology matching score has a possible value of between 0 and 100, a morphology matching score of 30 or less may indicate that the event is highly unlikely to be a true R-wave. In some cases, at least one true R-wave is expected to occur within an event cluster, e.g., as shown in FIG. 5A. In this case, at least one event in a detected cluster of sensed events may be required to have a morphology matching score greater than a match threshold, e.g., greater than 30, and all remaining events, which may be one or more, may be required to have morphology match score less than the threshold.

If the PWOS morphology criteria are not met at block 408, the sensed event cluster is not identified as PWOS. The cluster of sensed events may be a true arrhythmia or may be caused by other cardiac oversensing, e.g., T-wave oversensing, or other non-cardiac oversensing such as oversensing of electromagnetic interference, muscle noise, or other non-cardiac noise. If the PWOS morphology criteria are met at block 408, the sensed event cluster is identified as PWOS at block 410. The process of FIG. 10 may be repeated for each of the clusters that were counted toward reaching the cluster threshold. In other examples, clusters of sensed events are identified going forward in time after identifying one cluster as PWOS. Each cluster identified as being PWOS is counted at block 214 of FIG. 8 and if the PWOS counter reaches a threshold number of PWOS-identified clusters, a response to identifying the PWOS is provided as described above in conjunction with FIG. 8 and as described in conjunction with FIG. 11 below.

Figure 11:
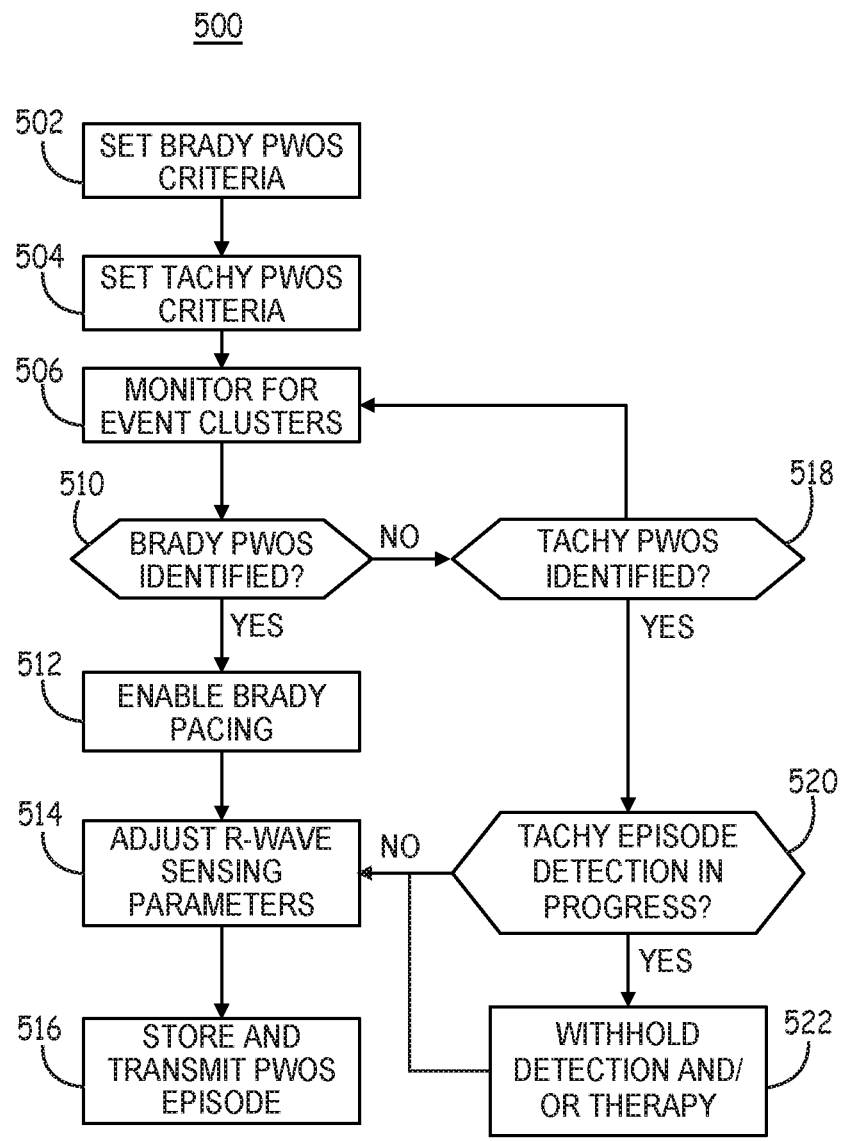
FIG. 11 is a flow chart of a method performed by the ICD of FIG. 1A for identifying and responding to PWOS according to another example.

FIG. 11 is a flow chart 500 of a method performed by ICD 14 for identifying and responding to PWOS according to one example. At block 502, bradycardia PWOS criteria are established and stored in memory 82 for access by control circuit 80 in detecting sensed event clusters and identifying PWOS during a bradycardia heart rhythm. At block 504, tachyarrhythmia PWOS criteria are established and stored for detecting sensed event clusters and identifying PWOS during tachyarrhythmia. PWOS may present a different pattern of sensed event clusters when the heart rhythm is slow, during bradycardia, than when the heart rhythm is fast, during tachycardia or fibrillation.

For example, the sensed event clusters during bradycardia may include a single short RRI when the sensed event pattern is an oversensed P-wave alternating with a sensed R-wave in a P-R-P-R pattern, which may persist over many cardiac cycles (multiple, sequential 2-event clusters) or over a few cardiac cycles with a series of intervening cardiac cycles with correctly sensed R-waves at normal RRIs and no oversensing. During a fast sensed heart rate, multiple P-waves may be oversensed for each true R-wave with none, one or more true R-waves sensed between sensed event clusters. Accordingly two or more different sets of PWOS detection criteria may be defined including different short and/or long interval thresholds used to detect clustered events, the number of short intervals required to detect a cluster, the number of sensed event clusters required to be identified before analyzing sensed event waveforms, the amplitude and/or morphology criteria used to identify PWOS in a sensed event cluster, and/or the number of clusters identified as PWOS required to provide a response to PWOS. Different criteria may be defined for detecting PWOS in the presence of bradycardia, in the presence of tachyarrhythmia, in the presence of AV conduction block or other conditions the patient may be known or expected to experience and which may influence the patterns of sensed events during PWOS.

After establishing at least two different sets of criteria, which may include establishing thresholds, an R-wave template and other criteria based on an analysis of the patient's cardiac electrical signal, control circuit 80 monitors for sensed event clusters according to the two (or more) sets of PWOS criteria. Sensed event signals and the cardiac electrical signal waveforms may be monitored for sensed event clusters according to multiple PWOS criteria simultaneously in order to detect different patterns of PWOS. Alternatively, the sensed event rate may be used to determine which set of PWOS criteria is actively being used. For example, if the sensed event rate over a predetermined number of sensed events, such as the most recent, 8, 12, 18, 22, or other number of sensed events is greater than a tachyarrhythmia detection rate, then the PWOS criteria for tachyarrhythmia established at block 504 are used. For example, if a running average RRI is less than 500 ms, less than a tachycardia detection interval, or if a tachyarrhythmia interval detection counter is greater than a predetermined number such as 3, the tachyarrhythmia PWOS criteria is used. If the heart rate is less than 120 beats per minute or a running average RRI is longer than the tachycardia detection interval and/or a tachyarrhythmia interval detection counter is inactive (at a count of zero), the bradycardia PWOS criteria may be used.

If PWOS is detected according to the bradycardia PWOS criteria, "yes" branch of block 510, one or more PWOS responses may be provided at block 512, 514 and/or 516. Bradycardia pacing may be enabled at block 512 in response to identifying PWOS based on the bradycardia PWOS criteria. A triggered pacing mode, e.g., VVT pacing mode, may be started to enable ventricular pacing at a rate that is faster than the intrinsic heart rate and is triggered from the next sensed event, which may be P-wave or an R-wave. A triggered pacing pulse is delivered by the therapy delivery circuit within a physiological refractory period of a sensed event, e.g., within 100 ms or within no more than 200 ms of the sensed event without setting a pacing escape interval upon sensing the event.

An inhibited pacing mode, e.g., VVI pacing mode, may be started at block 512 during which a sensed event signal inhibits a scheduled pacing pulse only if the sensed event is confirmed to be an R-wave. In an inhibited pacing mode, a pacing escape interval is started upon each sensed event (that occurs outside any device blanking or refractory periods). A pacing pulse is scheduled to be delivered if the pacing escape interval expires without being restarted due to another sensed event. Upon identifying PWOS and enabling bradycardia pacing, R-wave sensed event confirmation may be enabled at block 512 as part of the bradycardia pacing control. Before restarting the pacing escape interval in response to a sensed event, one or more morphology features may be determined for confirming each sensed event as being an R-wave. For example, the peak amplitude, positive going slope, morphology matching score or other morphological feature of each sensed event may be determined and compared to R-wave confirmation criteria. If the sensed event is confirmed to be an R-wave based on the confirmation criteria being satisfied, a running pacing escape interval is restarted in response to the confirmed R-wave so that the pacing pulse scheduled at the expiration of the escape interval is withheld. If the sensed event is not confirmed to be an R-wave, a running pacing escape interval is not restarted but is allowed to continue running until either a sensed event is confirmed to be an R-wave and the pacing escape interval is restarted or the pacing escape interval expires and the scheduled pacing pulse is delivered, whichever occurs first.

Alternatively or additionally, one or more parameters used to control the R-wave sensing threshold may be adjusted at block 514. For example, the R-wave sensing threshold starting value may be increased, a decay rate may be decreased, a time interval at which the sensing threshold is dropped to a lower value may be increased, the minimum sensing threshold may be increased, or other parameter may be adjusted to effectively increase the R-wave sensing threshold at the time the P-wave is expected to avoid PWOS on subsequent heart beats.

If PWOS is not being identified according to the bradycardia PWOS criteria but is being identified according to the tachyarrhythmia PWOS criteria, "yes" branch of block 518, ICD 14 may provide one or more responses to identifying the PWOS. For example if a tachyarrhythmia episode detection is in progress, as determined at block 520, detection of the tachyarrhythmia episode may be withheld and/or a VT or VF therapy may be withheld at block 522. A tachyarrhythmia episode detection may be determined to be in progress at block 520 if at least one tachyarrhythmia detection interval counter, e.g., a counter used to count the number of RRIs falling into a tachycardia interval zone or a counter used to count the number of RRIs falling into a fibrillation interval zone, is active, e.g., has a count that is greater than zero or another predetermined count.

Any time that PWOS is identified, control circuit 80 may respond at block 514 by adjusting R-wave sensing threshold control parameters to reduce the likelihood of oversensing of P-waves in the future. At block 516, ICD 14 may response to PWOS anytime it is identified by storing data relating to the identified PWOS in memory 82 for transmission to an external device 40 (FIG. 1) via telemetry circuit 88. Stored data may include a cardiac electrical signal including one or more sensed event clusters identified as PWOS, RRI data, morphology data, subsequent therapy delivered or withheld, or the like. Storage and transmission of data pertaining to the identified PWOS may enable a clinician to adjust programmed sensing parameters, PWOS detection criteria, tachyarrhythmia detection criteria, bradycardia pacing control parameters and/or tachyarrhythmia therapy control parameters to optimize the performance of ICD 14 in reliably determining the heart rhythm and delivering or withholding therapy as needed.

Figure 12:
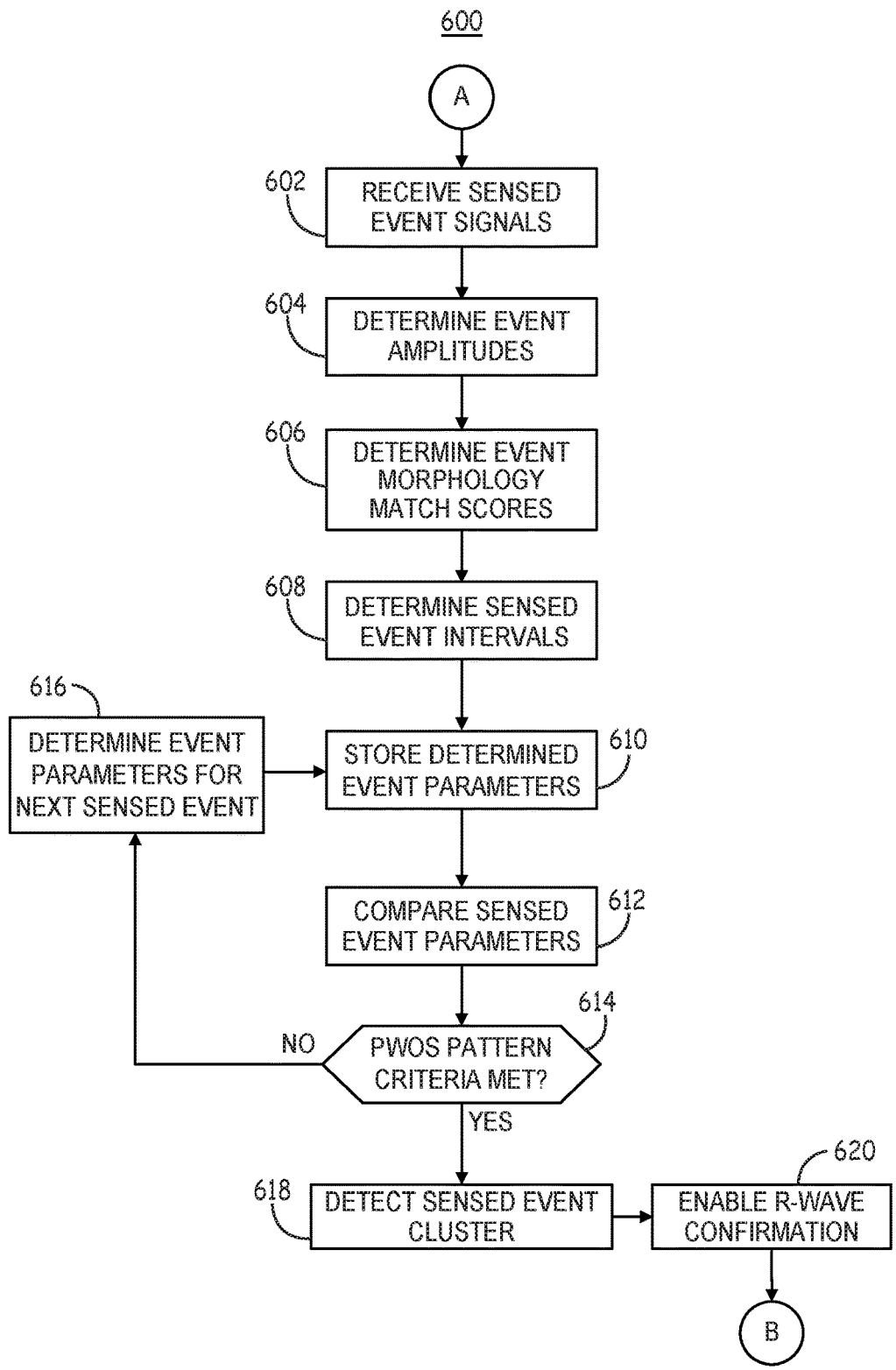
FIG. 12 is a flow chart of a method for identifying PWOS by an ICD according to another example.

FIG. 12 is a flow chart of a method for identifying PWOS by ICD 14 according to another example. At block 602, sensed event signals produced by sensing circuit 86 are received by control circuit 80. As the sensed event signals are received, the maximum peak amplitude of each sensed event is determined at block 604. In some examples, a blanking interval is started at the time that the cardiac electrical signal crosses the R-wave sensing threshold, such as blanking interval 172 shown in FIG. 5B. The control circuit 80 may determine the maximum sample point amplitude during the blanking interval 172 as the maximum peak amplitude of the respective sensed event.

At block 606, control circuit 80 determines a morphology matching score for each sensed event according to an implemented morphology matching scheme, such as any of the examples provided above and in the incorporated references. The morphology matching score is determined for each sensed event by comparing the waveform morphology or one or more morphology features of the cardiac signal waveform corresponding to the respective sensed event to a predetermined normal R-wave morphology template or normal R-wave features.

At block 608, the sensed event interval is determined as the time interval between two consecutive sensed event signals received at block 602. It is recognized that when the process of flow chart 600 first begins, a sensed event interval ending on the very first event sensed by sensing circuit 86 will not be determined since a most recent preceding sensed event will not exist. The very first event sensed by ICD 14 may be used, therefore, to set an initial time marker of the first sensed event to enable determination of the first sensed event interval ending with the second sensed event signal at block 608. The sensed event intervals determined at block 608 may be referred to herein as "RRIs" since they are determined based on R-wave sensed event signals, but the sensed event intervals may not be true "RRIs" since one (or both) of the sensed events defining the beginning and end of a sensed event interval may not be a true R-wave. For example, one or both sensed events may be an oversensed P-wave or other oversensed event.

These parameters (event amplitude, event morphology and event interval) may be determined at blocks 604, 606 and 608 for each sensed event as it occurs and stored in memory 82 at block 610. These three parameters determined for each sensed event may be used to determine if the sensed events are likely to include PWOS based on determined patterns of the successive event amplitudes, event morphologies and sensed event intervals.

At block 612, the control circuit 80 performs a comparative analysis of the sensed event parameters. In some examples, the event parameters for each event are first compared to a predetermined amplitude threshold, a predetermined morphology match threshold and a predetermined RRI threshold. In other examples, the analogous event parameters determined for each sensed event may be compared to each other. The comparative analysis is performed to determine if parameter values of consecutively sensed events represent a likely PWOS pattern. For instance, the comparative analysis may be performed to determine if consecutively sensed events includes groups of events that present an alternating pattern of low and high amplitude, R-wave and non-R-wave morphology, and/or short and long RRIs, which would be evidence of an alternating pattern of oversensed P-waves and true R-waves.

In one example, at block 612, the maximum peak amplitude determined for each sensed event may be compared to a maximum P-wave amplitude threshold, e.g., 1.5 mV. The maximum P-wave amplitude threshold may be a predetermined value based on empirical data or selected for the patient based on actual P-wave peak amplitude measurements (and/or R-wave peak amplitude measurements). If the event amplitude is less than the maximum P-wave amplitude threshold, the event may be labeled or flagged as a low amplitude event, "L." If the event amplitude is greater than the maximum P-wave amplitude threshold, the event may be labeled or flagged as a high amplitude event or "H."

Each sensed event interval may be compared to an RRI threshold at block 612. The RRI threshold may be a predetermined minimum event interval that would be considered a valid RRI when a tachyarrhythmia is not occurring, e.g., 300 ms. If the sensed event interval is less than the RRI threshold, the sensed event interval may be labeled as short or "S" and otherwise labeled as long or "L."

Additionally or alternatively at block 612, the morphology matching score for each event may be compared to an R-wave matching threshold. For example, the R-wave matching threshold may be 30 when the maximum possible matching score is 100. If the morphology matching score is less than the R-wave matching threshold, the event may be flagged or labeled as having a non-matching morphology, or "N," indicating that the sensed event is not likely to be an R-wave. If the morphology matching score is greater than 30 the event may be labeled or flagged as having a matching morphology, "M," indicating that the sensed event may be a true R-wave. Once at least three consecutive sensed events are labeled according to the three event parameters of amplitude, morphology and sensed event interval at which the event occurs, the three labels may be compared to determine if an event pattern indicative of PWOS is presented at block 614.

FIG. 14 is a timing diagram 700 of sensed event signals 702 that may be produced by sensing circuit 86 and received by control circuit 80. The sensed event signals 702 arrive in multiple sensed event clusters 711, 712, 713, 714, 715 and 716. Each cluster includes at least one oversensed P-wave (e.g., cluster 713) or multiple oversensed P-waves (e.g., cluster 714).

In response to each sensed event, control circuit 80 analyzes the digitized cardiac electrical signal and the time interval between consecutive sensed event signals to determine the maximum absolute peak amplitude of each event, a morphology matching score, and a sensed event interval as described above in conjunction with FIG. 12. Control circuit 80 may then label each event as having a high (H) or low (L) amplitude 704, having a non-matching (N) or matching (M) morphology matching score (MMS) 706, and as the ending event of a short (S) or long (L) RRI 708. This event parameter labeling may be based on comparisons to predetermined thresholds as described above in conjunction with FIG. 12.

Alternatively, the event labels may be determined based on comparing the event parameters to each other. For example, sensed event signals may be analyzed in pairs of two consecutive events, three consecutive events or groups of more than three consecutive sensed events, such as the group of four consecutive sensed events 720. The event having the highest amplitude within the group of consecutive sensed events may be identified and the amplitudes of each of the other events may be compared to the highest amplitude. The other event amplitudes that are less than a predetermined percentage of the highest amplitude are labeled as "L" for low amplitude. The other event amplitudes that are greater than a predetermined percentage of the highest event amplitude are labeled as "H" for high amplitude.

The highest morphology matching score may be identified and compared to the morphology matching scores of each of the other sensed events of the selected group of consecutive events, e.g., group 720. If the other morphology matching scores are greater than a predetermined percentage of the highest morphology matching score, the corresponding events are labeled "M" to indicate a morphology that is likely an R-wave. Any events of the selected group having morphology matching scores that are less than the predetermined percentage of the highest morphology matching score are labeled as non-matching or "N."

The longest RRI of the selected group of sensed events may be identified and compared to the other RRIs of the selected group. Events ending an RRI that is at least a predetermined percentage of the longest RRI are labeled as "L" (long). Events ending an RRI that is less than the predetermined percentage of the longest RRI are labeled as "S" (short).

In some examples, the sensed events may be labeled based on a combination of comparisons of event parameters to a predetermined threshold and comparisons to each other. For example, the RRIs may be compared to a predetermined threshold for labeling an event as occurring at a long or short interval. The highest morphology matching score may be determined and, as long as it is greater than a predetermined threshold, the corresponding event may be labeled as M (matching an R-wave morphology). Other event morphology matching scores may be compared to the same predetermined threshold or to a percentage of the highest morphology matching score. The maximum peak amplitude of the sensed event having the highest morphology matching score may be determined and the maximum P-wave sensing threshold may be set as a percentage of the maximum peak amplitude. The maximum peak amplitudes of the other sensed events of the selected group of events may be compared to the maximum P-wave sensing threshold determined based on the maximum amplitude of the event having the highest morphology matching score. Events having a peak amplitude less than the P-wave sensing threshold are labeled as "L" and event having a peak amplitude greater than the P-wave sensing threshold are labeled as "H." It is understood that other variations or combinations of comparisons of the event parameters to each other and/or to predetermined thresholds may be conceived and utilized for labeling the sensed events as being relatively low or high in amplitude, having a relatively low R-wave morphology matching score or a relatively high R-wave morphology matching score, and/or ending on a relatively short RRI or a relatively long RRI. The event labeling allows control module 80 to determine if a PWOS pattern is present.

Event labels for the parameters of amplitude 704, morphology matching score (MMS) 706 and RRI 708 are shown in timing diagram 700 for each sensed event signal 702. Control circuit 80 may analyze the sensed event labels for amplitude 704, MMS 706 and RRI 708 in running groups of four sensed events for identifying alternating patterns of L-H-L amplitude, N-M-N morphology matching scores, and S-L-S RRIs. For example, the first group of four sensed events 720 for which each of the parameters of amplitude, MMS and RRI are determined is selected for pattern analysis. An RRI is not determined for the very first sensed event signal 701. As such, a group of four consecutive sensed events 720 allows for the first three amplitude and morphology labels of the group of four sensed events to be examined and the last three event interval labels to be examined for an alternating PWOS pattern.

The amplitude labels and MMS labels for the first three sensed event signals of the first group of four sensed events 720 are shown in dashed boxes 705 and 707, respectively. The pattern of the amplitude and MMS labels are analyzed to determine if the first three sensed events of the group of four sensed events 720 occur in an alternating L-H-L and N-M-N pattern, respectively.

The RRI labels of the last three sensed events of the group of four sensed events 720 are shown in dashed box 709. The RRI labels of the last three sensed events of the group of four sensed events 720 correspond to the three respective RRIs that begin with the first three sensed events of the group of four sensed events 720. Control circuit 80 analyzes the RRI labels of the last three sensed events of the group of four sensed events 720 for an alternating pattern of S-L-S.

As can be seen in the example of FIG. 14, the first group of four sensed events 720 satisfies the criteria of an L-H-L amplitude pattern of the first three sensed events, an N-M-N morphology matching score pattern of the first three sensed events, and an S-L-S pattern of the RRI labels of the last three sensed events. As such, this group of four sensed events 720 is identified by the control circuit 80 as evidence of sensed event cluster 711 (and 712). In this example, the evidence of the L-H-L amplitude pattern, N-M-N morphology pattern, and S-L-S RRI pattern corresponds to the last short interval of sensed event cluster 711, the first short interval of sensed event cluster 712, and the intervening long sensed event interval 703 separating the two sensed event clusters 711 and 712. In response to identifying evidence of sensed event clusters 711 and 712, a PWOS cluster interval counter included in control circuit 80 may be increased by one. When the count of the PWOS cluster interval counter reaches a threshold, the control circuit 80 may provide a PWOS response, e.g., any of the responses described above in conjunction with FIGS. 8 and 11 or below in conjunction with FIG. 13.

After determining whether the first group of four sensed event intervals 720 present a pattern of PWOS as evidence of sensed event clusters, control module 80 may advance by one sensed event signal to the next group of four sensed events to analyze the next group of four consecutive sensed events, which in this example present H-L-L amplitude pattern, M-N-N morphology matching score pattern, and L-S-S RRI pattern. The next group of four sensed events is appropriately not identified as evidence of a new sensed event cluster since these events are still part of the sensed event clusters 711 and/or 712. In some examples, when a group of four sensed events is identified as evidence of sensed event clusters, the control circuit 80 may advance by two sensed events rather than only one sensed event to select the next group of four sensed events for analysis for a PWOS pattern. Advancement by only one sensed event may result in selecting four sensed events that still occur within the same two sensed event clusters that were just identified.

This process of selecting groups of four consecutive sensed events and analyzing the amplitude, MMS and RRI labels may continue until a threshold number of the groups of four sensed events are identified as being evidence of sensed event clusters. In the example shown, the groups of four sensed events 720, 722, 724, 726 and 728 are each identified as evidence of sensed event clusters 711 through 716 based on the L-H-L amplitude pattern, the N-M-N MMS pattern, and the S-L-S RRI pattern (each highlighted by respective dashed boxes for each group of four sensed events 720 through 728).

In each case, the sensed event clusters 701 through 716 are identified based on the last short interval of one cluster, the first short interval of the immediately following cluster, and the intervening long RRI. This analysis by control circuit 80 identifies the sensed event clusters 711 through 716 independent of the number of oversensed events and short RRIs occurring within each cluster 711 through 716. When the number of oversensed events and short RRIs within each cluster is variable, as shown in FIG. 14, the presence of the sensed event clusters is still identified without having to detect a threshold number of short RRIs within a cluster. The PWOS pattern may vary between patients and within a given patient as shown by the various examples of FIGS. 5B, 5C, 6 and 7. The techniques represented by FIG. 12 and FIG. 14 can be successfully implemented for identifying sensed event clusters due to PWOS without requiring prior knowledge of an anticipated or predicted number of events within the event clusters when PWOS occurs.

Returning to FIG. 12, if the PWOS pattern criteria are not met by the sensed event parameters based on the comparisons made at block 612, "no" branch of block 614, the control circuit 80 advances to block 616 to determine and store the next set of sensed event parameters upon receiving the next sensed event signal from sensing circuit 86.

If the comparisons of the sensed event parameters made at block 612 do meet PWOS pattern criteria, "yes" branch of block 614, a sensed event cluster is detected at block 618. The PWOS pattern criteria may require an alternating pattern of all three of the sensed event parameters determined for groups of consecutive events as described in conjunction with FIG. 14. In some cases, two out of the three sensed event parameters may be required to present an alternating pattern in order to satisfy the PWOS pattern criteria at block 614. For example, if the group of four consecutively sensed events present at least two of an L-H-L amplitude pattern, an N-M-N morphology matching score pattern, and an S-L-S RRI pattern, the PWOS pattern criteria may be satisfied at block 614. In some cases, as long as the S-L-S RRI pattern is detected, either an L-H-L amplitude pattern or an N-M-N morphology matching score pattern (or both) will satisfy the PWOS pattern criteria at block 614. In still other examples, an alternating patter of only one of the three sensed event parameters within the group of four consecutively sensed events may satisfy the PWOS pattern criteria at block 614.

In the example of FIG. 12, if the PWOS pattern criteria are met a single time, a sensed event cluster is detected at block 618, and the control circuit 80 enables R-wave confirmation at block 620 for use in controlling therapy delivery. In other examples, a threshold number of sensed event cluster detections may be required based on the PWOS pattern criteria being met multiple times before enabling R-wave confirmation at block 620.

Figure 13:
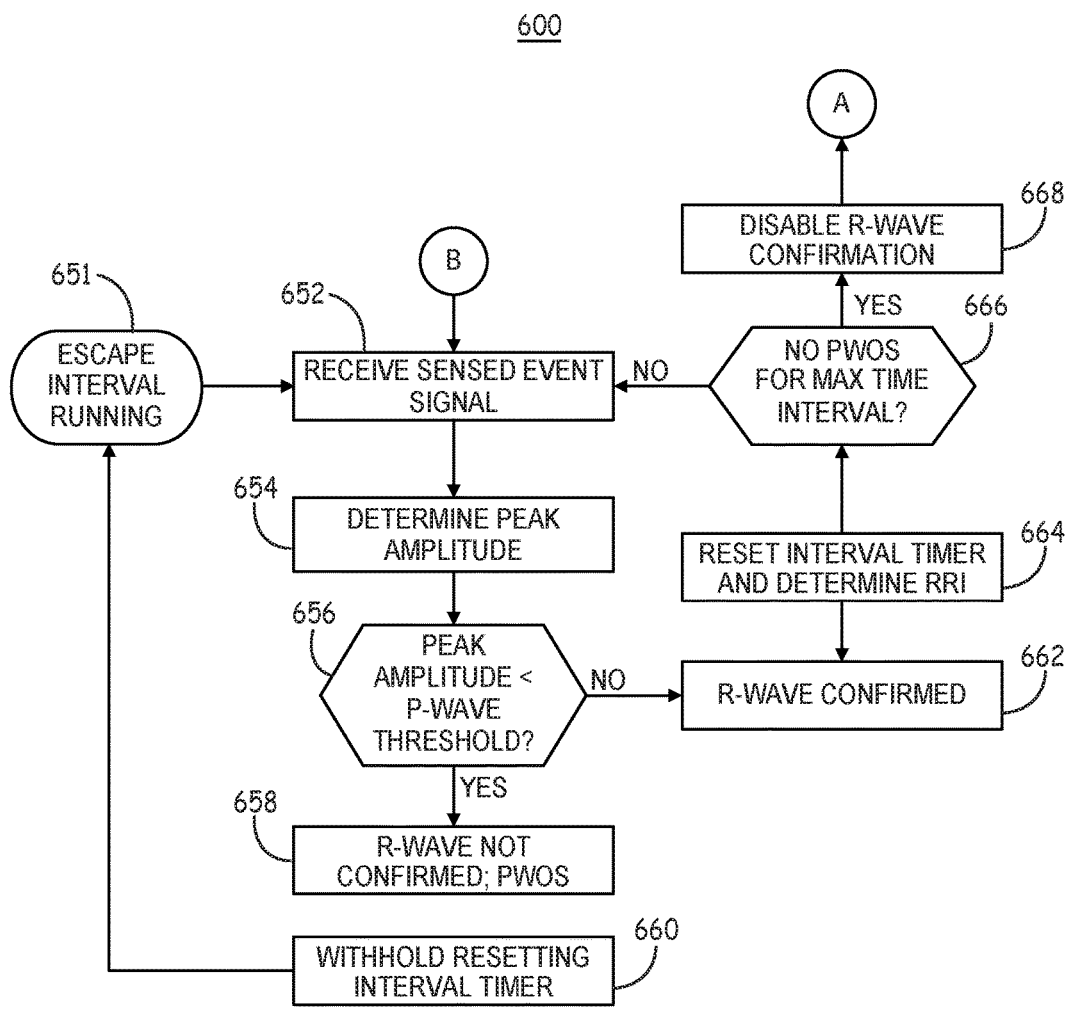
FIG. 13 is a flow chart of a method for confirming R-waves after identifying PWOS.

FIG. 13 is a continuation of flow chart 600. If R-wave confirmation is enabled at block 620 of FIG. 12, control circuit 80 advances to block 652 of FIG. 14 (as indicated by connector "B") to wait for the next sensed event signal at block 652. Control circuit 80 switches from monitoring for PWOS as described in conjunction with FIG. 12 and FIG. 14 to performing R-wave confirmation as shown by the method of FIG. 13 to identify PWOS events on a beat-to-beat basis and reduce the likelihood of an improper withholding or delivery of therapy due to PWOS. As indicated by block 651, the pacer timing and control circuitry of control circuit 80 may be running an escape interval timer or counter that was started upon the immediately preceding sensed event signal. As described above in conjunction with FIG. 4, the escape interval timer may be started for timing out a pacing time interval for controlling the timing of pacing pulse delivery. The escape interval timer may be restarted in response to a sensed event signal from sensing circuit 86 and the value of the timer may be used for determining the sensed event interval since the immediately preceding sensed event. The sensed event interval may be used both for PWOS detection as described in conjunction with FIGS. 12 and 14 and for detecting tachyarrhythmia, e.g., according to VT and VF detection algorithms.

At block 654, control circuit 80 determines the maximum peak amplitude of the currently sensed event, sensed t block 652 after R-wave confirmation is enabled. The peak amplitude is compared to a P-wave amplitude threshold at block 656. If the peak amplitude of the sensed event is less than the P-wave amplitude threshold, "yes" branch of block 656, control circuit 80 may identify the sensed event as being a PWOS event at block 658 or at least does not confirm the sensed event as being an R-wave. Resetting of the running escape interval is withheld at block 660. The currently running escape interval timer is allowed to continue running at block 651 without being reset due to the sensed event signal. In this way, the PWOS event does not interfere with the scheduling and timing of pacing pulses or the detection of a tachyarrhythmia.

For instance, a bradycardia pacing escape interval may be started by control circuit 80 in response to the most recent preceding sensed event signal. This running escape interval is allowed to continue to run without being reset so that the PWOS event does not prevent bradycardia pacing when it is needed. The PWOS does not cause the escape interval to be reset which may otherwise lead to a false RRI determination that may be less than a pacing interval and lead to withholding of a pacing pulse, or the false RRI may be in a tachycardia or fibrillation interval range and lead toward a false tachyarrhythmia detection.

If the peak amplitude is greater than the P-wave amplitude threshold, "no" branch of block 656, the sensed event is confirmed to be an R-wave at block 662. A pacing escape interval timer is reset at block 664 in response to the confirmed R-wave. It is to be understood that when the escape interval timer is reset, the time expired on the escape interval timer is used as a determination of the RRI ending on the confirmed R-wave, and this RRI may be used by tachyarrhythmia detection algorithms implemented in ICD 14. It is also to be understood that if the escape interval expires before a confirmed R-wave causes the escape interval to be restarted, a pacing pulse may be delivered by ICD 14.

In some examples, control circuit 80 may determine at block 666 if no PWOS events have been identified over a predetermined maximum time interval. If PWOS has not been identified for a predetermined maximum time interval, e.g., for one minute, 5 minutes, one hour, 24 hours, or other desired interval, control circuit switches back to the PWOS monitoring mode by returning to block 602 of FIG. 12 (as indicated by connector "A"). In this way, a beat-by-beat confirmation of R-waves is not performed if PWOS is not detected for the predetermined maximum time interval set for controlling how long R-wave confirmation takes place on a beat-by-beat basis in the absence of PWOS detection.

Alternatively, if PWOS is detected at least once, before or after enabling R-wave confirmation, the ICD 14 may remain in the monitoring mode in which all sensed events are analyzed to confirm whether or not the event is a true R-wave until ICD 14 is reprogrammed by a user. In some examples, the R-wave confirmation mode described in conjunction with FIG. 13 may be entered directly at block 652 without requiring PWOS monitoring to be performed first as described in conjunction with FIG. 12.

Enabling the PWOS monitoring mode only (FIG. 12), enabling the R-wave confirmation mode only (FIG. 13) and enabling the PWOS monitoring mode with automatic switching to the R-wave confirmation mode (combination of FIGS. 12 and 13) may be user-programmable features of ICD 14. When the PWOS monitoring mode as described in conjunction with FIGS. 12 and 14 is enabled without automatic switching to the R-wave confirmation mode in response to one or a higher predetermined number of sensed event clusters being identified, the ICD 14 may respond to a predetermined number of sensed event clusters being identified during the monitoring mode by recording a cardiac electrical signal segment including identified PWOS, adjusting R-wave sensing threshold control parameters, withholding a tachyarrhythmia episode detection and/or therapy, delivering one or more triggered pacing pulses within the physiological refractory period of one or more respective sensed events to provide bradycardia pacing support if needed, or any combination of these responses or other PWOS responses described herein.

Thus, a method and apparatus for identifying and responding to PWOS in an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An implantable cardioverter defibrillator (ICD) system, comprising:
    a sensing circuit configured to:
        receive a cardiac electrical signal from electrodes coupled to the ICD, and
        sense a plurality of consecutive cardiac events from the cardiac electrical signal, each one of the plurality of consecutive cardiac events being sensed as an R-wave in response to the cardiac electrical signal crossing an R-wave sensing threshold;
    a therapy delivery circuit configured to deliver electrical stimulation therapy to a patient's heart via electrodes coupled to the ICD; and
    a control circuit configured to:
        determine at least one sensed event parameter from the cardiac electrical signal for each one of the plurality of consecutive cardiac events sensed as an R-wave by the sensing circuit;
        compare the sensed event parameters to P-wave oversensing criteria;
        detect P-wave oversensing in response to the sensed event parameters meeting the P-wave oversensing criteria, the P-wave oversensing corresponding to at least one P-wave being falsely sensed as at least one of the plurality of consecutive cardiac events that is sensed as an R-wave by the sensing circuit; and
        adjust at least one of an R-wave sensing control parameter or a therapy delivery control parameter in response to detecting the P-wave oversensing.

2. The system of claim 1, wherein the control circuit is configured to:
    determine the at least one sensed event parameter by determining event time intervals between the plurality of consecutive cardiac events;
    compare the event time intervals to at least a first time interval threshold;
    detect a cluster of sensed events based on at least a threshold number of the event intervals being less than the first time interval threshold and at least one of the event intervals being greater than the first time interval threshold and consecutive with the threshold number of event intervals ; and
    detect the P-wave oversensing in response to detecting the cluster of sensed events.

3. The system of claim 2, wherein the control circuit is further configured to detect the P-wave oversensing by:
    comparing the cluster of cardiac events to the P-wave oversensing criteria; and
    identifying the cluster of cardiac events as P-wave oversensing when the cluster of cardiac events meets the P-wave oversensing criteria.

4. The system of claim 2, wherein the control circuit is further configured to:
    determine if a threshold number of clusters of cardiac events is detected based on determining time intervals between sensed cardiac events;

determine at least one morphology feature of each the detected clusters of sensed events in response to the threshold number of clusters of cardiac events being detected;

compare the at least one morphology feature to P-wave oversensing criteria; and identify each cluster of cardiac events having the at least one morphology feature meeting the P-wave oversensing criteria as P-wave oversensing.

5. The system of claim 2, wherein the control circuit is configured to:

determine a maximum peak amplitude of each of the detected clusters of cardiac events;

compare the maximum peak amplitude to an amplitude threshold; and identify each detected cluster of cardiac events having the maximum peak amplitude less than the amplitude threshold as P-wave oversensing.

6. The system of claim 2, wherein the control circuit is further configured to:

determine a morphology match score between each of the sensed events of each detected cluster of cardiac events and a previously determined R-wave template;

compare each morphology match score to a match score threshold; and identify each cluster of cardiac events having at least a predetermined portion of the determined morphology match scores for the respective cluster of cardiac events being less than a match score threshold.

7. The system of claim 2, wherein the control circuit is further configured to:

determine a peak amplitude from the cardiac electrical signal for each of the plurality of consecutive cardiac events;

determine a morphology matching score for each of the plurality of consecutive cardiac events by comparing the cardiac electrical signal to a pre-determined R-wave template;

determine a first pattern of the peak amplitudes determined for the consecutive cardiac events by labeling each of the peak amplitudes as one of high or low based on a comparison of the peak amplitudes to an amplitude threshold;

determine a second pattern of the morphology matching scores determined for the consecutive cardiac events by labeling each of the morphology matching scores as one of match or non-match based on a comparison of the morphology matching scores to an R-wave matching threshold;

determine a third pattern of the event time intervals determined for the consecutive cardiac events by labeling each of the event time intervals as one of short or long based on a comparison of the event time intervals to the event interval threshold; and detect the cluster of sensed events based on at least one of the first pattern, the second pattern and the third pattern being an alternating pattern.

8. The system of claim 1, further comprising a memory coupled to the control circuit and a telemetry circuit comprising a transceiver for transmitting and receiving data from an external medical device, the control circuit further configured to store cardiac electrical signal data in the memory in response to identifying the P-wave oversensing and control the telemetry circuit to transmit the stored cardiac electrical signal data to the external medical device.

9. The system of claim 1, wherein the P-wave oversensing criteria comprises a first set of P-wave oversensing criteria and a second set of P-wave oversensing criteria, and the control circuit is configured to:

detect and identify a first cluster of cardiac events sensed by the sensing circuit based on the first set of P-wave oversensing criteria;

detect and identify a second cluster of cardiac events sensed by the sensing circuit based on the second set of P-wave oversensing criteria;

control the therapy delivery circuit to provide one of a first therapy response in response to identifying the first cluster of cardiac events or a second therapy response in response to identifying the second cluster of cardiac events, the first therapy response different than the second therapy response.

10. The system of claim 9, wherein the first therapy response comprises delivering at least one bradycardia pacing pulse, and the second therapy response comprises withholding delivery of a tachyarrhythmia therapy.

11. The system of claim 1, wherein the control circuit is configured to:

adjust the therapy control parameter by enabling R-wave confirmation in response to identifying the P-wave oversensing;

set a bradycardia pacing escape interval;

compare the cardiac electrical signal to R-wave confirmation criteria in response to the sensing circuit sensing a cardiac event;

reset the pacing escape interval in response to confirming the sensed cardiac event as being an R-wave based on comparing the cardiac electrical signal to the R-wave confirmation criteria;

allow the pacing escape interval to continue running in response to not confirming the sensed cardiac event as being an R-wave based on comparing the cardiac electrical signal to the R-wave confirmation criteria.

12. The system of claim 1, wherein the control circuit is configured to:

detect a tachyarrhythmia episode based on the cardiac electrical signal;

reject the tachyarrhythmia episode detection in response to identifying the P-wave oversensing.

13. The system of claim 1, wherein the control circuit is further configured to:

determine the at least one sensed event parameter by determining a maximum peak amplitude of the cardiac electrical signals corresponding to each cardiac event sensed by the sensing circuit;

compare the sensed event parameters to the P-wave oversensing criteria by comparing the maximum peak amplitude determined for each sensed event to a maximum P-wave amplitude threshold; and detect the P-wave oversensing in response to the maximum peak amplitude of a sensed cardiac event being less than the P-wave amplitude threshold.

14. The system of claim 13, wherein the control circuit is further configured to:

set an interval timer in response to the sensing circuit sensing a cardiac event;

reset the interval timer in response to the maximum peak amplitude being greater than the maximum P-wave amplitude threshold; and allow the interval timer to continue running in response to the maximum peak amplitude being less than the maximum P-wave amplitude threshold.

15. The system of claim 14, wherein the control circuit is configured to set the interval timer to a pacing escape interval and control the therapy delivery circuit to deliver a pacing pulse in response to the interval timer expiring.

16. The system of claim 1, further comprising an extra-cardiovascular lead carrying at least one of the electrodes coupled to the ICD.

17. A method comprising:
receiving a cardiac electrical signal;
sensing a plurality of consecutive cardiac events from the cardiac electrical signal, each one of the plurality of consecutive cardiac events being sensed as an R-wave in response to the cardiac electrical signal crossing an R-wave sensing threshold;
determining at least one sensed event parameter from the cardiac electrical signal for each one of the plurality of consecutive sensed cardiac events;
comparing the sensed event parameters to P-wave oversensing criteria;
detecting P-wave oversensing in response to the sensed event parameters meeting the P-wave oversensing criteria, the P-wave oversensing corresponding to at least one P-wave being falsely sensed as at least one of the plurality of consecutive cardiac events that is sensed as an R-wave by the sensing circuit; and
adjusting at least one of an R-wave sensing control parameter or a therapy delivery control parameter in response to detecting the P-wave oversensing.

18. The method of claim 17, further comprising
determining the at least one sensed event parameter by determining event time intervals between the plurality of consecutive cardiac events;
comparing the event time intervals to at least a first time interval threshold;
detecting a cluster of sensed events based on at least a threshold number of the event intervals being less than the first time interval threshold and at least one of the event intervals being greater than the first time interval threshold and consecutive with the threshold number of event intervals; and
detecting the P-wave oversensing based on detecting the cluster of sensed events.

19. The method of claim 18, further comprising detecting the P-wave
oversensing by: comparing the cluster of cardiac events to the P-wave
oversensing criteria; and
identifying the cluster of cardiac events as P-wave oversensing when the cluster of cardiac events meets the P-wave oversensing criteria.

20. The method of claim 18, further comprising:
determining if a threshold number of clusters of cardiac events is detected based on determining time intervals between sensed cardiac events;
determining at least one morphology feature of each the detected clusters of sensed events in response to the threshold number of clusters of cardiac events being detected;
comparing the at least one morphology feature to P-wave oversensing criteria; and
identifying each cluster of cardiac events having the at least one morphology feature meeting the P-wave oversensing criteria as P-wave oversensing.

21. The method of claim 18, further comprising:
determining a maximum peak amplitude of each of the detected clusters of cardiac events;
comparing the maximum peak amplitude to an amplitude threshold; and
identifying each detected cluster of cardiac events having the maximum peak amplitude less than the amplitude threshold as P-wave oversensing.

22. The method of claim 18, further comprising:
determining a morphology match score between each of the sensed events of each detected cluster of cardiac events and a previously determined R-wave template;
comparing each morphology match score to a match score threshold; and
identifying each cluster of cardiac events having at least a predetermined portion of the determined morphology match scores for the respective cluster of cardiac events being less than a match score threshold.

23. The method of claim 17, further comprising:
storing cardiac electrical signal data in a memory in response to identifying the P-wave oversensing; and
transmitting the stored cardiac electrical signal data to an external medical device.

24. The method of claim 17, further comprising:
storing in the memory the P-wave oversensing criteria comprising a first set of P-wave oversensing criteria and a second set of P-wave oversensing criteria;
detecting and identifying a first cluster of sensed cardiac events based on the first set of P-wave oversensing criteria;
detecting and identifying a second cluster of sensed cardiac events based on the second set of P-wave oversensing criteria;
providing one of a first therapy response in response to identifying the first cluster of cardiac events or a second therapy response in response to identifying the second cluster of cardiac events, the first therapy response different than the second therapy response.

25. The method of claim 24, wherein the first therapy response comprises delivering at least one bradycardia pacing pulse, and the second therapy response comprises withholding delivery of a tachyarrhythmia therapy.

26. The method of claim 17, further comprising:
wherein adjusting the therapy control parameter comprises enabling R-wave confirmation in response to identifying the P-wave oversensing;
setting a bradycardia pacing escape interval;
comparing the cardiac electrical signal to R-wave confirmation criteria in response to sensing a cardiac event;
resetting the pacing escape interval in response to confirming the sensed cardiac event as being an R-wave based on comparing the cardiac electrical signal to the R-wave confirmation criteria; and
allowing the pacing escape interval to continue running in response to not confirming the sensed cardiac event as being an R-wave based on comparing the cardiac electrical signal to the R-wave confirmation criteria.

27. The method of claim 17, further comprising:
detecting a tachyarrhythmia episode based on the cardiac electrical signal;
rejecting the tachyarrhythmia episode detection in response to identifying the P-wave oversensing.

28. The method of 17, further comprising:
determining a peak amplitude from the cardiac electrical signal for each of the plurality of consecutive cardiac events;
determining a morphology matching score for each of the plurality of consecutive cardiac events by comparing the cardiac electrical signal to a pre-determined R-wave template;

determining a first pattern of the peak amplitudes determined for the consecutive cardiac events by labeling each of the peak amplitudes as one of high or low based on a comparison of the peak amplitudes to an amplitude threshold;

determining a second pattern of the morphology matching scores determined for the consecutive cardiac events by labeling each of the morphology matching scores as one of match or non-match based on a comparison of the morphology matching scores to an R-wave matching threshold;

determining a third pattern of the event time intervals determined for the consecutive cardiac events by labeling each of the event time intervals as one of short or long based on a comparison of the event time intervals to the event interval threshold; and detecting the cluster of sensed events based on at least two of the first pattern, the second pattern and the third pattern being an alternating pattern.

29. The method of claim 17, further comprising:

determining the at least one sensed event parameter by determining a maximum peak amplitude of the cardiac electrical signals corresponding to each sensed cardiac event;

comparing the sensed event parameters to the P-wave oversensing criteria by comparing the maximum peak amplitude determined for each sensed event to a maximum P-wave amplitude threshold; and detecting the P-wave oversensing in response to the maximum peak amplitude of a sensed cardiac event being less than the P-wave amplitude threshold.

30. The method of claim 29, further comprising:

setting an interval timer in response to a cardiac event;

resetting the interval timer in response to the maximum peak amplitude being greater than the maximum P-wave amplitude threshold; and allowing the interval timer to continue running in response to the maximum peak amplitude being less than the maximum P-wave amplitude threshold.

31. The method of claim 30, wherein setting the interval times comprises setting the interval timer to a pacing escape interval, the method further comprising delivering a pacing pulse in response to the interval timer expiring.

32. A non-transitory, computer-readable storage medium comprising a set of instructions which, when executed by a control circuit of a medical system, cause the system to:

receive a cardiac electrical signal by a sensing circuit via electrodes coupled to the medical system;

sense a plurality of consecutive cardiac events from the cardiac electrical signal, each one of the plurality of consecutive cardiac events being sensed as an R-wave in response to the cardiac electrical signal crossing an R-wave sensing threshold;

determine by a control circuit of the medical system at least one sensed event parameter from the cardiac electrical signal for each one of the plurality of consecutive cardiac events sensed as an R-wave by the sensing circuit;

compare the sensed event parameters to P-wave oversensing criteria;

detect P-wave oversensing in response to the sensed event parameters meeting the P-wave oversensing criteria, the P-wave oversensing corresponding to at least one P-wave being falsely sensed as at least one of the plurality of consecutive cardiac events that is sensed as an R-wave by the sensing circuit; and adjust at least one of an R-wave sensing control parameter or a therapy delivery control parameter in response to detecting the P-wave oversensing.

* * * * *